(12) United States Patent
Earl et al.

(10) Patent No.: US 9,592,127 B2
(45) Date of Patent: Mar. 14, 2017

(54) DISTAL FEMORAL KNEE PROSTHESES

(75) Inventors: Brian D. Earl, South Bend, IN (US);
Abraham P. Habegger, Milford, IN (US); Aaron A. Hoffman, Salt Lake City, UT (US); Kim C. Bertin, Bountiful, UT (US); Lawrence Dorr, La Canada, CA (US); Robert E. Booth, Jr., Philadelphia, PA (US); Aaron Rosenberg, Deerfield, IL (US); Sergio Romagnoli, Savona (IT)

(73) Assignee: Zimmer, Inc., Warsaw, IN (US)

( * ) Notice: Subject to any disclaimer, the term of this patent is extended or adjusted under 35 U.S.C. 154(b) by 992 days.

(21) Appl. No.: 11/611,021

(22) Filed: Dec. 14, 2006

(65) Prior Publication Data
US 2007/0260323 A1 Nov. 8, 2007

Related U.S. Application Data

(60) Provisional application No. 60/750,613, filed on Dec. 15, 2005, provisional application No. 60/805,933, filed on Jun. 27, 2006.

(51) Int. Cl.
*A61F 2/38* (2006.01)
*A61F 2/30* (2006.01)
(52) U.S. Cl.
CPC .. *A61F 2/3859* (2013.01); *A61F 2002/30616* (2013.01)
(58) Field of Classification Search
CPC .................................................. A61F 2/3859
(Continued)

(56) References Cited

U.S. PATENT DOCUMENTS

| 4,081,866 A | 4/1978 | Upshaw et al. |
| 4,340,978 A | 7/1982 | Buechel et al. |

(Continued)

FOREIGN PATENT DOCUMENTS

| AU | 2006325787 B2 | 10/2013 |
| CN | 101642394 A | 2/2010 |

(Continued)

OTHER PUBLICATIONS

Article: Anthropometric Measurements of the Human Knee: Correlation to the Sizing of Current Knee Arthroplasty Systems, Kirby Hitt et al., The Journal of Bone & Joint Surgery (2003), pp. 114-122 (Hitt).

(Continued)

*Primary Examiner* — Thomas J Sweet
*Assistant Examiner* — Megan Wolf
(74) *Attorney, Agent, or Firm* — Schwegman Lundberg & Woessner, P.A.

(57) ABSTRACT

A set of distal femoral knee prostheses which are designed to be more narrow in medial/lateral dimensions with increasing anterior/posterior size than existing prostheses to more closely correspond to the physical anatomy of female patients. The prostheses are designed to have a substantially trapezoidal shape or profile when viewed distally which features a more pronounced narrowing of the medial/lateral dimensions beginning at the posterior end of the prostheses and progressing anteriorly to the anterior end of the prostheses. Additionally, the prostheses each include a reduced profile patellar sulcus and reduced profile anterior condyles to more closely conform to the anatomy of a resected femur, and also include sulcus tracking optimized to conform to female anatomy.

18 Claims, 20 Drawing Sheets

(58) Field of Classification Search
USPC .......................................... 623/20.14–20.36
See application file for complete search history.

(56) References Cited

U.S. PATENT DOCUMENTS

| | | | |
|---|---|---|---|
| 4,662,889 A * | 5/1987 | Zichner et al. ............ | 623/20.26 |
| 4,888,020 A | 12/1989 | Horber | |
| 4,944,756 A | 7/1990 | Kenna | |
| 5,061,271 A | 10/1991 | Van Zile | |
| 5,133,758 A | 7/1992 | Hollister | |
| 5,137,536 A | 8/1992 | Koshino | |
| 5,226,915 A | 7/1993 | Bertin | |
| 5,282,861 A | 2/1994 | Kaplan | |
| 5,326,361 A | 7/1994 | Hollister | |
| 5,330,532 A * | 7/1994 | Ranawat ............... | A61F 2/3886 623/20.27 |
| 5,445,642 A | 8/1995 | McNulty et al. | |
| 5,549,686 A | 8/1996 | Johnson et al. | |
| 5,549,688 A | 8/1996 | Ries et al. | |
| 5,609,643 A | 3/1997 | Colleran et al. | |
| 5,681,354 A * | 10/1997 | Eckhoff .................... | 623/20.35 |
| 5,688,279 A * | 11/1997 | McNulty et al. .............. | 606/88 |
| 5,728,162 A | 3/1998 | Eckhoff | |
| 5,776,201 A | 7/1998 | Colleran et al. | |
| 5,824,105 A | 10/1998 | Ries et al. | |
| 5,871,546 A | 2/1999 | Colleran et al. | |
| 5,935,173 A | 8/1999 | Roger et al. | |
| 6,013,103 A | 1/2000 | Kaufman et al. | |
| 6,039,764 A | 3/2000 | Pottenger et al. | |
| 6,152,960 A | 11/2000 | Pappas | |
| 6,197,064 B1 * | 3/2001 | Haines et al. ............. | 623/20.31 |
| 6,217,619 B1 | 4/2001 | Keller | |
| 6,235,060 B1 | 5/2001 | Kubein-Meesenburg et al. | |
| 6,264,697 B1 | 7/2001 | Walker | |
| 6,325,828 B1 | 12/2001 | Dennis et al. | |
| 6,364,911 B1 | 4/2002 | Schmotzer et al. | |
| 6,540,786 B2 | 4/2003 | Chibrac et al. | |
| 6,540,787 B2 | 4/2003 | Biegun et al. | |
| 6,589,283 B1 | 7/2003 | Metzger et al. | |
| 6,616,696 B1 | 9/2003 | Merchant | |
| 6,699,291 B1 | 3/2004 | Augoyard et al. | |
| 6,712,856 B1 * | 3/2004 | Carignan et al. .......... | 623/20.35 |
| 6,770,099 B2 | 8/2004 | Andriacchi et al. | |
| 6,802,865 B2 | 10/2004 | Biegun et al. | |
| 6,846,329 B2 | 1/2005 | Mcminn | |
| 6,893,467 B1 | 5/2005 | Bercovy | |
| 7,081,137 B1 | 7/2006 | Servidio | |
| 7,306,609 B2 | 12/2007 | Schmotzer et al. | |
| 7,364,590 B2 | 4/2008 | Siebel | |
| 7,413,577 B1 | 8/2008 | Servidio | |
| 7,678,152 B2 | 3/2010 | Suguro et al. | |
| 7,695,520 B2 | 4/2010 | Metzger et al. | |
| 7,806,897 B1 | 10/2010 | Bonutti | |
| 8,062,377 B2 | 11/2011 | Haines | |
| 8,075,626 B2 | 12/2011 | Dun | |
| 8,088,167 B2 | 1/2012 | Haines | |
| 8,298,288 B2 | 10/2012 | Walker | |
| 8,357,202 B2 | 1/2013 | Heggendorn et al. | |
| 8,377,141 B2 | 2/2013 | Mcminn | |
| 8,394,147 B2 | 3/2013 | Otto et al. | |
| 8,409,293 B1 | 4/2013 | Howard et al. | |
| 8,480,753 B2 | 7/2013 | Collazo et al. | |
| 8,480,754 B2 | 7/2013 | Bojarski et al. | |
| 8,500,816 B2 | 8/2013 | Dees, Jr. et al. | |
| 8,551,179 B2 | 10/2013 | Jones et al. | |
| 8,721,732 B2 | 5/2014 | Samuelson et al. | |
| 9,173,744 B2 | 11/2015 | Donno et al. | |
| 9,308,095 B2 | 4/2016 | Parisi et al. | |
| 2003/0158606 A1 | 8/2003 | Coon et al. | |
| 2003/0225458 A1 | 12/2003 | Donkers et al. | |
| 2004/0039450 A1 | 2/2004 | Griner et al. | |
| 2004/0172137 A1 | 9/2004 | Blaylock et al. | |
| 2004/0249467 A1 | 12/2004 | Meyers et al. | |
| 2005/0102032 A1 | 5/2005 | Beynnon et al. | |
| 2005/0107884 A1 | 5/2005 | Johnson et al. | |
| 2005/0177169 A1 | 8/2005 | Fisher et al. | |
| 2005/0283249 A1 | 12/2005 | Carson | |
| 2005/0283250 A1 | 12/2005 | Coon et al. | |
| 2005/0283251 A1 | 12/2005 | Coon et al. | |
| 2005/0283252 A1 | 12/2005 | Coon et al. | |
| 2005/0283253 A1 | 12/2005 | Coon et al. | |
| 2006/0129246 A1 | 6/2006 | Steffensmeier | |
| 2006/0224244 A1 | 10/2006 | Thomas et al. | |
| 2006/0235541 A1 | 10/2006 | Hodorek | |
| 2006/0235542 A1 | 10/2006 | Hodorek | |
| 2006/0287733 A1 | 12/2006 | Bonutti | |
| 2007/0088444 A1 | 4/2007 | Hodorek et al. | |
| 2007/0123984 A1 | 5/2007 | Hodorek | |
| 2007/0135926 A1 | 6/2007 | Walker | |
| 2007/0179607 A1 | 8/2007 | Hodorek et al. | |
| 2007/0233269 A1 | 10/2007 | Steines et al. | |
| 2008/0058947 A1 | 3/2008 | Earl et al. | |
| 2008/0058948 A1 | 3/2008 | Biegun et al. | |
| 2008/0097616 A1 | 4/2008 | Meyers et al. | |
| 2008/0119940 A1 | 5/2008 | Otto et al. | |
| 2008/0140212 A1 | 6/2008 | Metzger et al. | |
| 2008/0188855 A1 | 8/2008 | Brown et al. | |
| 2008/0188937 A1 | 8/2008 | Ribic | |
| 2008/0188942 A1 | 8/2008 | Brown et al. | |
| 2008/0243258 A1 | 10/2008 | Sancheti | |
| 2008/0281428 A1 | 11/2008 | Meyers et al. | |
| 2008/0288080 A1 | 11/2008 | Sancheti | |
| 2009/0036992 A1 | 2/2009 | Tsakonas | |
| 2009/0043395 A1 | 2/2009 | Hotokebuchi et al. | |
| 2009/0062924 A1 | 3/2009 | Kito et al. | |
| 2009/0105772 A1 | 4/2009 | Seebeck et al. | |
| 2009/0132055 A1 | 5/2009 | Ferro | |
| 2009/0222103 A1 | 9/2009 | Fitz et al. | |
| 2009/0265011 A1 | 10/2009 | Mandell | |
| 2009/0265013 A1 | 10/2009 | Mandell | |
| 2009/0306786 A1 | 12/2009 | Samuelson | |
| 2009/0306787 A1 | 12/2009 | Crabtree et al. | |
| 2009/0319047 A1 | 12/2009 | Walker | |
| 2009/0319048 A1 | 12/2009 | Shah et al. | |
| 2009/0319049 A1 | 12/2009 | Shah et al. | |
| 2009/0326663 A1 | 12/2009 | Dun | |
| 2009/0326665 A1 | 12/2009 | Wyss et al. | |
| 2009/0326666 A1 | 12/2009 | Wyss et al. | |
| 2009/0326667 A1 | 12/2009 | Williams et al. | |
| 2010/0036499 A1 | 2/2010 | Pinskerova | |
| 2010/0036500 A1 | 2/2010 | Heldreth et al. | |
| 2010/0042224 A1 | 2/2010 | Otto et al. | |
| 2010/0161067 A1 | 6/2010 | Saleh et al. | |
| 2010/0191298 A1 | 7/2010 | Earl et al. | |
| 2010/0305708 A1 | 12/2010 | Lang et al. | |
| 2010/0329530 A1 | 12/2010 | Lang et al. | |
| 2011/0022179 A1 | 1/2011 | Andriacchi et al. | |
| 2011/0093083 A1 | 4/2011 | Earl et al. | |
| 2011/0144760 A1 | 6/2011 | Wong et al. | |
| 2011/0218541 A1 | 9/2011 | Bailey et al. | |
| 2011/0307067 A1 | 12/2011 | Dees | |
| 2012/0203350 A1 | 8/2012 | Hagen et al. | |
| 2012/0310362 A1 | 12/2012 | Li et al. | |
| 2012/0323334 A1 | 12/2012 | Jones et al. | |
| 2012/0323335 A1 | 12/2012 | Parisi et al. | |
| 2012/0323336 A1 | 12/2012 | Parisi et al. | |
| 2012/0323337 A1 | 12/2012 | Parisi et al. | |
| 2013/0006370 A1 | 1/2013 | Wogoman et al. | |
| 2013/0006371 A1 | 1/2013 | Wogoman et al. | |
| 2013/0006376 A1 | 1/2013 | Wogoman et al. | |
| 2013/0006378 A1 | 1/2013 | Wogoman | |
| 2013/0035765 A1 | 2/2013 | Dacus | |
| 2013/0197653 A1 | 8/2013 | Hawkins et al. | |
| 2013/0226305 A1 | 8/2013 | Donno et al. | |
| 2014/0128973 A1 | 5/2014 | Howard et al. | |
| 2014/0142713 A1 | 5/2014 | Wright et al. | |
| 2015/0374500 A1 | 12/2015 | Donno et al. | |

FOREIGN PATENT DOCUMENTS

| | | |
|---|---|---|
| CN | 102076283 A | 5/2011 |
| CN | 101330883 B | 3/2013 |
| CN | 103732186 A | 4/2014 |
| DE | 202007014128 U1 | 1/2008 |

(56) References Cited

FOREIGN PATENT DOCUMENTS

| | | | |
|---|---|---|---|
| EP | 0303467 | A2 | 2/1989 |
| EP | 0376658 | B1 | 6/1994 |
| EP | 0381352 | B1 | 6/1994 |
| EP | 0567705 | B1 | 7/1997 |
| EP | 0993812 | A2 | 4/2000 |
| EP | 1013232 | A2 | 6/2000 |
| EP | 1285638 | A2 | 2/2003 |
| EP | 1033117 | B1 | 6/2004 |
| EP | 0975286 | B1 | 8/2004 |
| EP | 1477142 | A2 | 11/2004 |
| EP | 1477143 | A1 | 11/2004 |
| EP | 1285638 | B1 | 11/2005 |
| EP | 1719478 | A2 | 11/2006 |
| EP | 1722721 | A1 | 11/2006 |
| EP | 1354571 | B1 | 6/2007 |
| EP | 1862150 | A1 | 12/2007 |
| EP | 2004099 | A2 | 12/2008 |
| EP | 1867302 | B1 | 9/2009 |
| EP | 2147660 | A1 | 1/2010 |
| EP | 2158878 | A1 | 3/2010 |
| EP | 1555962 | B1 | 2/2011 |
| EP | 2324799 | A2 | 5/2011 |
| EP | 2335654 | A1 | 6/2011 |
| EP | 2720646 | A1 | 4/2014 |
| FR | 2901996 | A1 | 12/2007 |
| JP | 3267055 | A | 11/1991 |
| JP | 0553501 | A | 3/1993 |
| JP | 0568987 | A | 3/1993 |
| JP | 9-149908 | A | 6/1997 |
| JP | 11504226 | A | 4/1999 |
| JP | 11511347 | A | 10/1999 |
| JP | 3469972 | B2 | 11/2003 |
| JP | 3495161 | B2 | 2/2004 |
| JP | 2004166802 | A | 6/2004 |
| JP | 2005532089 | A | 10/2005 |
| JP | 2009519781 | A | 5/2009 |
| JP | 4820547 | B2 | 11/2011 |
| JP | 5571863 | B1 | 7/2014 |
| JP | 2014522292 | A | 9/2014 |
| WO | WO-9535074 | A1 | 12/1995 |
| WO | WO-9603939 | A1 | 2/1996 |
| WO | WO-0023010 | A1 | 4/2000 |
| WO | WO03/094782 | A2 | 11/2003 |
| WO | WO-2004016204 | A1 | 2/2004 |
| WO | WO-2005037147 | A1 | 4/2005 |
| WO | WO-2005051240 | A1 | 6/2005 |
| WO | WO-2005122967 | A1 | 12/2005 |
| WO | WO-2006058057 | A2 | 6/2006 |
| WO | WO2007/054553 | A1 | 5/2007 |
| WO | WO-2007070859 | A2 | 6/2007 |
| WO | WO-2007109641 | A2 | 9/2007 |
| WO | WO-2008054389 | A1 | 5/2008 |
| WO | WO-2009088234 | A2 | 7/2009 |
| WO | WO-2009088236 | A2 | 7/2009 |
| WO | WO-2009088238 | A2 | 7/2009 |
| WO | WO-2009105495 | A1 | 8/2009 |
| WO | WO-2010108550 | A1 | 9/2010 |
| WO | WO-2011072235 | A2 | 6/2011 |
| WO | WO-2012031774 | A1 | 3/2012 |
| WO | WO-2012112698 | A2 | 8/2012 |
| WO | WO-2012173704 | A1 | 12/2012 |
| WO | WO-2012173706 | A1 | 12/2012 |
| WO | WO-2012173740 | A1 | 12/2012 |

OTHER PUBLICATIONS

Article: Dimensions of the Knee—Radiographic and autopsy study of sizes required for a knee prosthesis, B.B. Seedhom et al., Annals of the Rheumatic Diseases (1972), pp. 54-58 (Seedhom).

Article: Knee Morphology as a Guide to Knee Replacement, Joseph S. Mensch et al., Clinical Orthopaedics and Related Research No. 112, Oct. 1975, pp. 231-241 (Mensch).

Article: Rotational Landmarks and Sizing of the Distal Femur in Total Knee Arthroplasty, Pascal L. Poilvache, MD. et al., Clinical Orthopaedics and Related Research, No. 331 (1996), pp. 35-46 (Poilvache).

Article: The Anatomy and Funcational Axes of the Femur, Yuki Yoshioka, MD. et al., The Journal of Bone and Joint Surgery, vol. 69A, No. 6, Jul. 1987, pp. 873-880 (Yoshioka).

Complaint of W. Norman Scott and Giles R. Scuderi filed, Sep. 9, 2010 in the US District Court of Delaware in Case No. 10-772-GMS.

Answer filed Dec. 1, 2010 of Zimmer, Inc. and Zimmer Technology, Inc. in the US District Court of Delaware in Case No. 10-772-GMS.

Office Action mailed Feb. 4, 2010 in related U.S. Appl. No. 11/780,248.

Response filed May 3, 2010 in related U.S. Appl. No. 11/611,021.

Office Action mailed Jul. 21, 2010 in related U.S. Appl. No. 11/780,248.

"U.S. Appl. No. 12/974,018, Final Office Action mailed Apr. 13, 2012", 11 pgs.

"U.S. Appl. No. 12/974,018, Non Final Office Action mailed Nov. 10, 2011", 5 pgs.

"U.S. Appl. No. 12/974,018, Preliminary Amendment filed Dec. 21, 2010", 4 pgs.

"U.S. Appl. No. 12/974,018, Response filed Mar. 8, 2012 to Non Final Office Action mailed Nov. 10, 2011", 12 pgs.

"U.S. Appl. No. 12/974,018, Response filed Oct. 12, 2012 to Final Office Action mailed Apr. 13, 2012", 16 pgs.

"U.S. Appl. No. 13/161,624, Notice of Allowance mailed Mar. 12, 2013", 11 pgs.

"U.S. Appl. No. 13/161,624, Response filed Feb. 26, 2013 to Restriction Requirement mailed Sep. 26, 2012", 9 pgs.

"U.S. Appl. No. 13/161,624, Restriction Requirement mailed Sep. 26, 2012", 8 pgs.

"U.S. Appl. No. 13/459,060, Preliminary Amendment filed Apr. 27, 2012", 6 pgs.

"U.S. Appl. No. 13/459,061, Preliminary Amendment filed Apr. 27, 2012", 6 pgs.

"U.S. Appl. No. 13/459,064, Preliminary Amendment filed Apr. 27, 2012", 6 pgs.

"Australian Application Serial No. 2006325787, Office Action mailed Mar. 14, 2012", 2 pgs.

"Australian Application Serial No. 2006325787, Office Action mailed Nov. 14, 2011", 2 pgs.

"Australian Application Serial No. 2006325787, Response filed Feb. 21, 2012 to Office Action mailed Nov. 14, 2011", 34 pgs.

"Chinese Application Serial No. 200680046893, Office Action mailed Aug. 3, 2012", (W/ English Translation), 8 pgs.

"Chinese Application Serial No. 200680046893, Office Action mailed Aug. 10, 2010", (W/ English Translation), 22 pgs.

"Chinese Application Serial No. 200680046893, Office Action mailed Dec. 6, 2011", (W/ English Translation), 5 pgs.

"Chinese Application Serial No. 200680046893, Response filed Jan. 23, 2012 to Office Action mailed Dec. 6, 2011", (W/ English Translation), 11 pgs.

"Chinese Application Serial No. 200680046893.7, Response filed Oct. 17, 2012 to Office Action mailed Aug. 3, 2012", (W/ English Translation), 8 pgs.

"Extramedullary/Intramedullary Tibial Resector: Surgical Technique", Nexgen Complete Knee Solution, Zimmer, Inc. 97-5997-02 Rev 1, (2000, 2002), 25 pgs.

"Gender Solutions Natural-Knee Flex System", Zimmer, Inc., (2007, 2009), 6 pgs.

"Gender Solutions Natural-Knee Flex System: Surgical Technique", Zimmer, Inc., (2007, 2008, 2009), 36 pgs.

"Gender Solutions Patello-Femoral Joint (PFJ) System: Surgical Technique", Zimmer Inc., (2008, 2009), 38 pgs.

"International Application Serial No. PCT/EP2011/004556, International Preliminary Report on Patentability mailed Mar. 12, 2013", 9 pgs.

"International Application Serial No. PCT/EP2011/004556, International Search Report mailed Feb. 9, 2012", 6 pgs.

"International Application Serial No. PCT/EP2011/004556, Written Opinion mailed Mar. 12, 2013", 9 pgs.

(56) References Cited

OTHER PUBLICATIONS

"International Application Serial No. PCT/US2012/035688, Partial Search Report mailed Jul. 3, 2012", 8 pgs.
"International Application Serial No. PCT/US2012/035688, Search Report mailed Sep. 17, 2012", 7 pgs.
"International Application Serial No. PCT/US2012/035688, Written Opinion mailed Sep. 17, 2012", 11 pgs.
"International Application Serial No. PCT/US2012/035691, Partial Search Report mailed Jul. 10, 2012", 8 pgs.
"International Application Serial No. PCT/US2012/035691, Written Opinion mailed Sep. 17, 2012", 11 pgs.
"International Application Serial No. PCT/US2012/035693, Partial Search Report mailed Jun. 27, 2012", 8 pgs.
"International Application Serial No. PCT/US2012/035693, Search Report mailed Oct. 9, 2012", 7 pgs.
"International Application Serial No. PCT/US2012/035693, Written Opinion mailed Oct. 9, 2012", 11 pgs.
"International Application Serial No. PCT/US2012/038531, Search Report mailed Oct. 8, 2012", 14 pgs.
"International Application Serial No. PCT/US2012/038531, Written Opinion mailed Oct. 8, 2012", 10 pgs.
"Japanese Application Serial No. 2008-545981, Examiners Decision of Final Refusal mailed Oct. 16, 2012", (W/ English Translation), 3 pgs.
"Japanese Application Serial No. 2008-545981, Office Action mailed Apr. 17, 2012 ", (W/ English Translation), 5 pgs.
"Japanese Application Serial No. 2008-545981, Office Action mailed Jul. 5, 2011", (W/ English Translation), 13 pgs.
"Japanese Application Serial No. 2008-545981, Response filed Oct. 5, 2011 to Office Action mailed Jul. 5, 2011", (W/ English Translation), 6 pgs.
"Japanese Application Serial No. 2008-545981, Response filed Aug. 30, 2012 to Office Action mailed Apr. 17, 2012", (W/ English Translation), 5 pgs.
"Japanese Application Serial No. 2011-221305, Office Action mailed Feb. 26, 2013", (W/ English Translation), 13 pgs.
"Japanese Application Serial No. 2011-221305, Office Action mailed Sep. 17, 2013", (W/ English Translation), 5 pgs.
"Japanese Application Serial No. 2011-221305, Response filed Aug. 26, 2013 to Office Action mailed Feb. 26, 2013", (W/ English Translation), 9 pgs.
"LPS-Flex Fixed Bearing Knee: Surgical Technique", Zimmer, Inc., (2004, 2007, 2008), 16 pgs.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"Surgical Technique for the CR-Flex Fixed Bearing Knee", NexGen Complete Knee Solution, Zimmer, Inc., (2003), 22 pgs.
"Unicompartmental High Flex Knee: Intramedullary, Spacer Block Option and Extramedullary Minimally Invasive Surgical Techniques", Zimmer, Inc., (2004, 2009, 2010), 62 pgs.
U.S. Appl. No. 11/780,248, filed Jul. 19, 2007, Distal Femoral Knee Prostheses.
U.S. Appl. No. 12/974,018, filed Dec. 21, 2010, Distal Femoral Knee Prostheses.
U.S. Appl. No. 13/819,528, filed May 13, 2013, Femoral Prosthesis With Medicalized Patellar Groove.
U.S. Appl. No. 13/459,060, filed Apr. 27, 2012, Femoral Component for a Knee Prosthesis With Improved Articular Characteristics.
"U.S. Appl. No. 12/974,018, Non Final Office Action mailed Apr. 4, 2014", 11 pgs.
"U.S. Appl. No. 13/459,060, Non Final Office Action mailed Mar. 14, 2014", 8 pgs.
"U.S. Appl. No. 13/459,060, Response filed Jan. 3, 2014 to Restriction Requirement mailed Nov. 4, 2013", 25 pgs.
"U.S. Appl. No. 13/459,060, Response filed Jul. 14, 2014 to Non-Final Office Action dated Mar. 14, 2014", 30 pgs.
"U.S. Appl. No. 13/459,060, Restriction Requirement mailed Nov. 4, 2013", 6 pgs.
"U.S. Appl. No. 13/819,528, Non Final Office Action mailed Dec. 6, 2013", 15 pgs.
"U.S. Appl. No. 13/819,528, Response filed May 22, 2014 to Non Final Office Action mailed Dec. 6, 2013", 15 pgs.
"U.S. Appl. No. 61/381,803, filed Sep. 10, 2010", 23 pgs.
"Australian Application Serial No. 2006325787, Response filed May 3, 2013 to Office Action mailed Mar. 14, 2012", 10 pgs.
"Australian Application Serial No. 2012271153, Amendment filed Jan. 16, 2014", 13 pgs.
"Canadian Application Serial No. 2,641,966, Office Action mailed Feb. 6, 2014", 2 pgs.
"Canadian Application Serial No. 2,641,966, Office Action mailed Jul. 16, 2013", 2 pgs.
"Canadian Application Serial No. 2,641,966, Response filed Jan. 15, 2014 to Office Action mailed Jul. 16, 2013", 6 pgs.
"European Application Serial No. 06840269.2, Examination Notification Art. 94(3) mailed Jan. 24, 2014", 6 pgs.
"International Application Serial No. PCT/US2012/035691, Search Report mailed Sep. 17, 2012", 7 pgs.
"International Application Serial No. PCT/US2012/035693, International Preliminary Report on Patentability mailed Jan. 3, 2014", 13 pgs.
"Japanese Application Serial No. 2011-221305, Response filed Dec. 17, 2013 to Office Action mailed Sep. 17, 2013", (W/ English Translation of Claims), 8 pgs.
"Japanese Application Serial No. 2014-515821, Request for Examination Amendment filed Apr. 8, 2014", (W/ English Translation), 18 pgs.
"U.S. Appl. No. 12/974,018, Response filed Jul. 30, 2014 to Non-Final Office Action mailed Apr. 4, 2014", 15 pgs.
"U.S. Appl. No. 12/974,018, Appeal Brief filed Feb. 20, 2015", 24 pgs.
"U.S. Appl. No. 12/974,018, Final Office Action mailed Oct. 10, 2014", 12 pgs.
"U.S. Appl. No. 13/459,060, Non Final Office Action mailed Oct. 9, 2014", 11 pgs.
"U.S. Appl. No. 13/459,060, Response filed Feb. 18, 2015 to Non-Final Office Action mailed Oct. 9, 2014", 23 pgs.
"U.S. Appl. No. 13/819,528, Final Office Action mailed Feb. 5, 2015", 15 pgs.
"U.S. Appl. No. 13/819,528, Non Final Office Action mailed Aug. 12, 2014", 10 pgs.
"U.S. Appl. No. 13/819,528, Response filed Jan. 12, 2015 to Non Final Office Action mailed Aug. 12, 2014", 13 pgs.
"Canadian Application Serial No. 2,641,966, Office Action mailed Aug. 25, 2014", 2 pgs.
"European Application Serial No. 06840269.2, Examination Notification Art. 94(3) mailed Nov. 12, 2014", 4 pgs.
"U.S. Appl. No. 13/459,060, Advisory Action mailed Jun. 8, 2015", 3 pgs.
"U.S. Appl. No. 13/459,060, Final Office Action mailed Apr. 1, 2015", 11 pgs.
"U.S. Appl. No. 13/459,060, Response filed May 28, 2015 to Final Office Action mailed Apr. 1, 2015", 21 pgs.
"U.S. Appl. No. 13/819,528, Advisory Action mailed Apr. 14, 2015", 3 pgs.
"U.S. Appl. No. 13/819,528, Notice of Allowance mailed Jun. 22, 2015", 7 pgs.
"U.S. Appl. No. 13/819,528, Preliminary Amendment filed Feb. 27, 2013", 9 pgs.
"U.S. Appl. No. 13/819,528, Response filed Apr. 2, 2015 to Final Office Action mailed Feb. 5, 2015", 12 pgs.
"U.S. Appl. No. 13/819,528, Response filed Apr. 29, 2015 to Advisory Action mailed Apr. 14, 2015", 13 pgs.
"U.S. Appl. No. 13/819,528, Supplemental Preliminary Amendment filed Jul. 11, 2013 ", 6 pgs.
"Canadian Application Serial No. 2,641,966, Response filed Feb. 25, 2015 to Office Action mailed Aug. 25, 2014", 4 pgs.
"Canadian Application Serial No. 2,641,966, Response filed Aug. 6, 2014 to Office Action mailed Feb. 6, 2014", 3 pgs.

(56) References Cited

OTHER PUBLICATIONS

"Chinese Application Serial No. 201280039703.4, Office Action mailed Mar. 30, 2015", (W/ English Translation), 2 pgs.

"Chinese Application Serial No. 201280039703.4, Office Action mailed May 28, 2015", (W/ English Translation), 12 pgs.

"European Application Serial No. 06840269.2, Response filed Mar. 23, 2015 to Examination Notification Art. 94(3) mailed Nov. 12, 2014", 10 pgs.

"European Application Serial No. 06840269.2, Response filed Aug. 4, 2014 to Examination Notification Art. 94(3) mailed Jan. 24, 2014", 10 pgs.

"International Application Serial No. PCT/US2006/062117, International Preliminary Report on Patentability mailed on Jun. 18, 2008", 5 pgs.

"International Application Serial No. PCT/US2006/062117, Written Opinion mailed on Apr. 5, 2007", 4 pgs.

"U.S. Appl. No. 13/459,060, Notice of Allowance mailed Dec. 7, 2015", 7 pgs.

"U.S. Appl. No. 14/845,522, Preliminary Amendment filed Sep. 24, 2015", 7 pgs.

1 "Canadian Application Serial No. 2,641,966, Office Action mailed Sep. 4, 2015", 4 pgs.

"Chinese Application Serial No. 201280039703.4, Response filed Sep. 7, 2015 to Office Action mailed May 28, 2015", (W/ English Translation), 72 pgs.

U.S. Appl. No. 14/845,522, filed Sep. 4, 2015, Femoral Prosthesis With Medicalized Patellar Groove.

"U.S. Appl. No. 13/459,060, PTO Response to Rule 312 Communication mailed Mar. 3, 2016", 2 pgs.

"U.S. Appl. No. 14/845,522, Non Final Office Action mailed Jun. 1, 2016", 11 pgs.

"U.S. Appl. No. 15/092,107, Preliminary Amendment filed Apr. 7, 2016", 11 pgs.

"Australian Application Serial No. 2013245552, First Examiner Report mailed Mar. 30, 2016", 4 pgs.

"Chinese Application Serial No. 201280039703.4, Response filed May 31, 2016 to Office Action mailed May 10, 2016", (W/ English Translation), 34 pgs.

"European Application Serial No. 06840269.2, Decision to Grant mailed Feb. 18, 2016", 3 pgs.

"European Application Serial No. 06840269.2, Office Action mailed Sep. 8, 2015", 67 pgs.

* cited by examiner

FIG_3

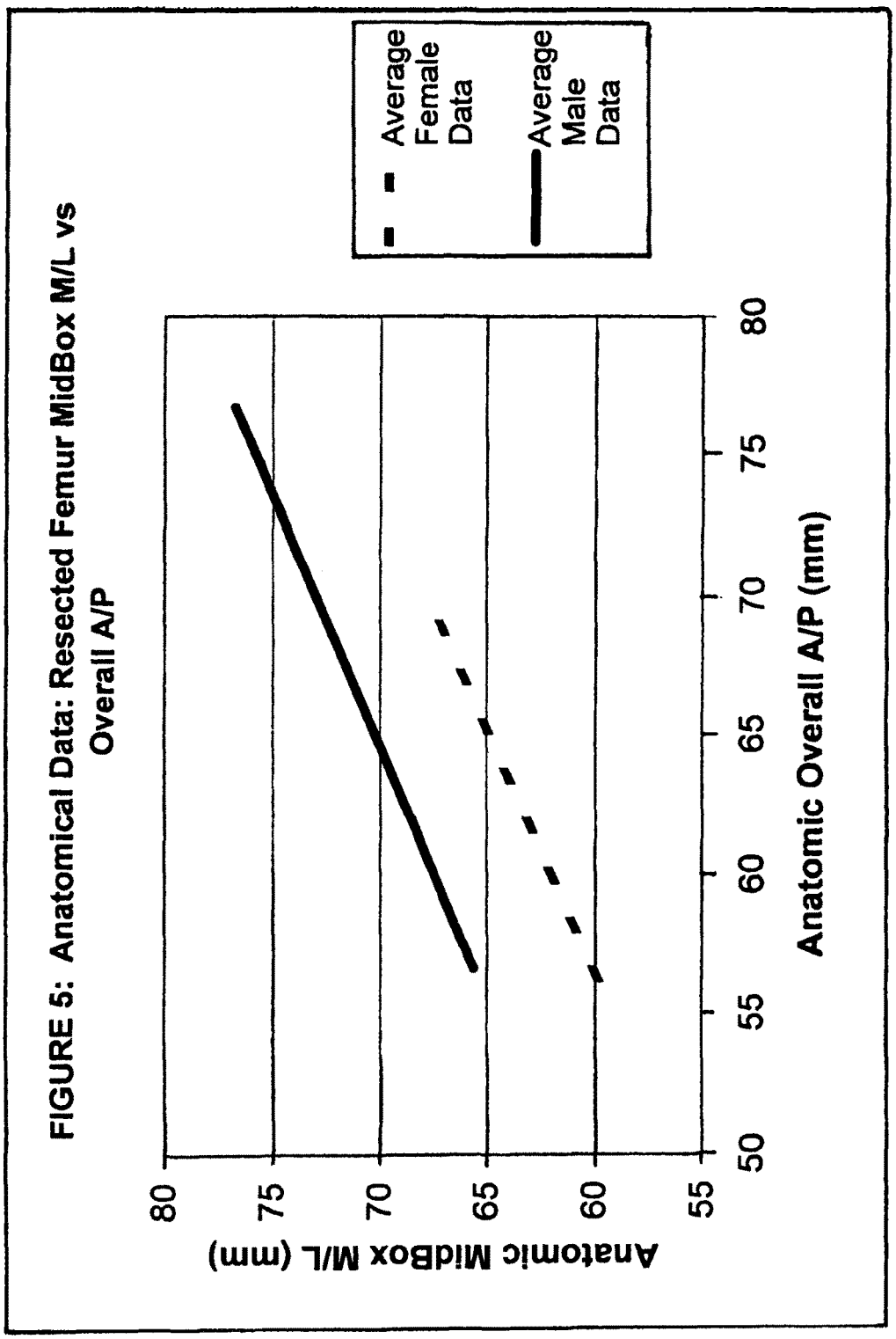

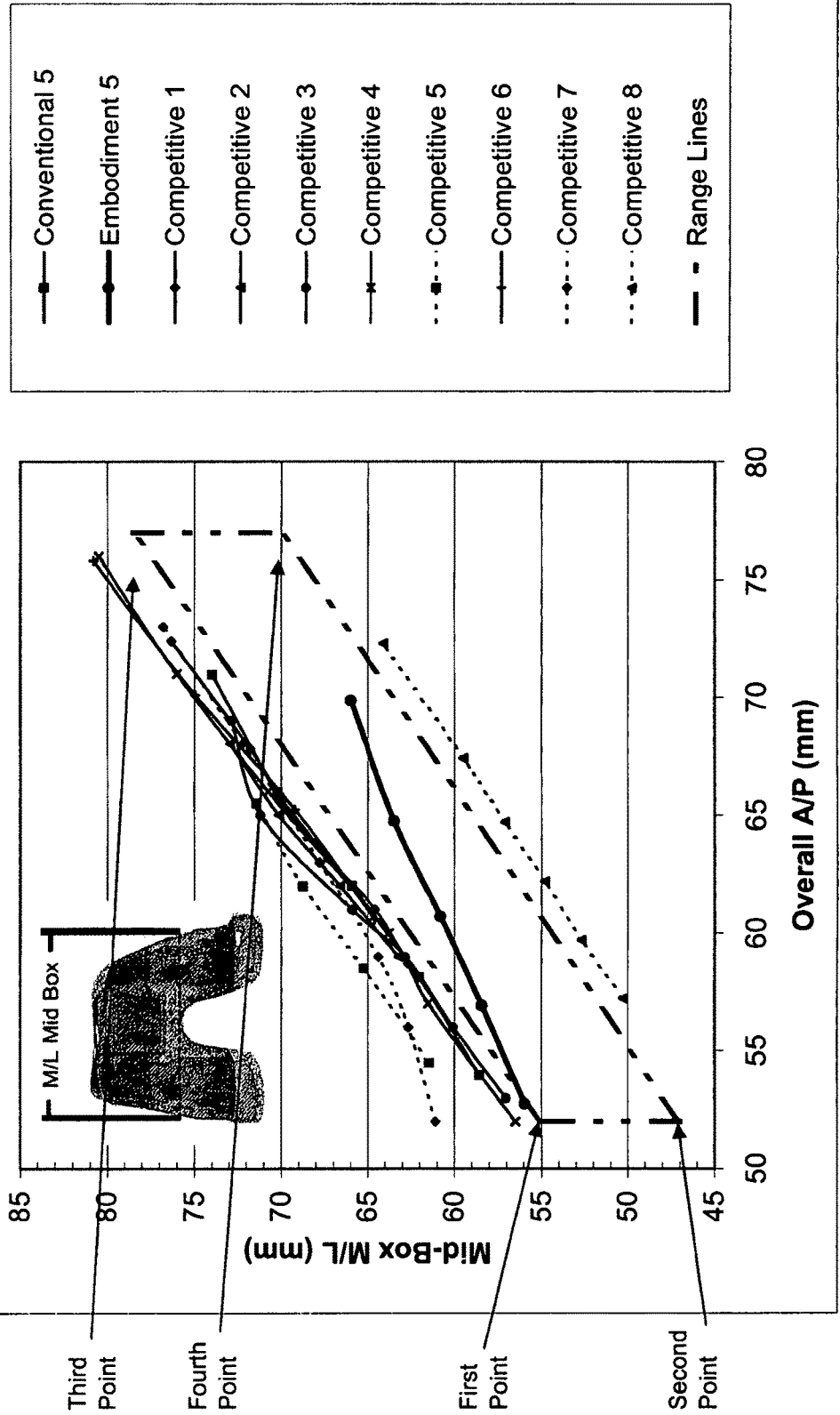

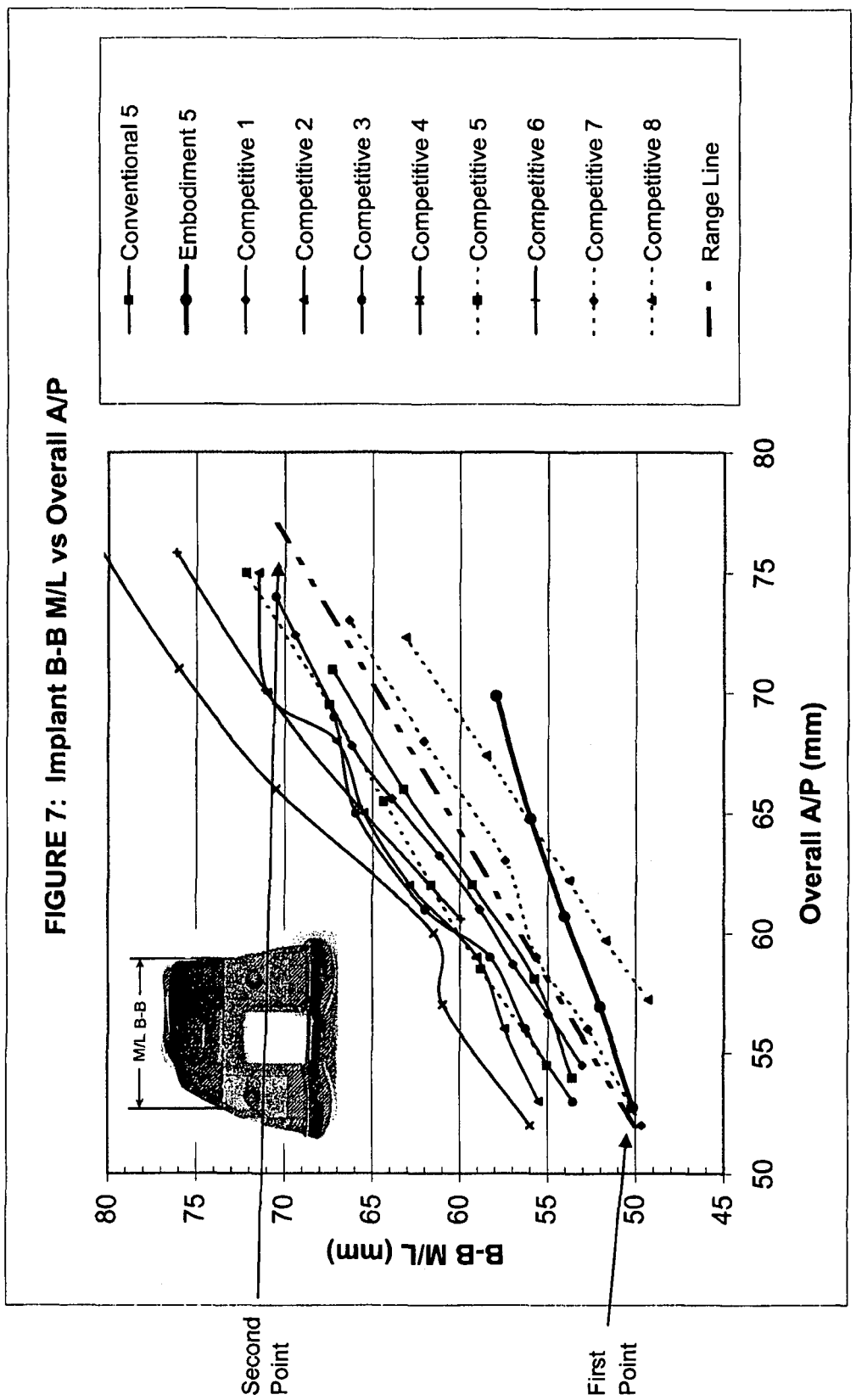

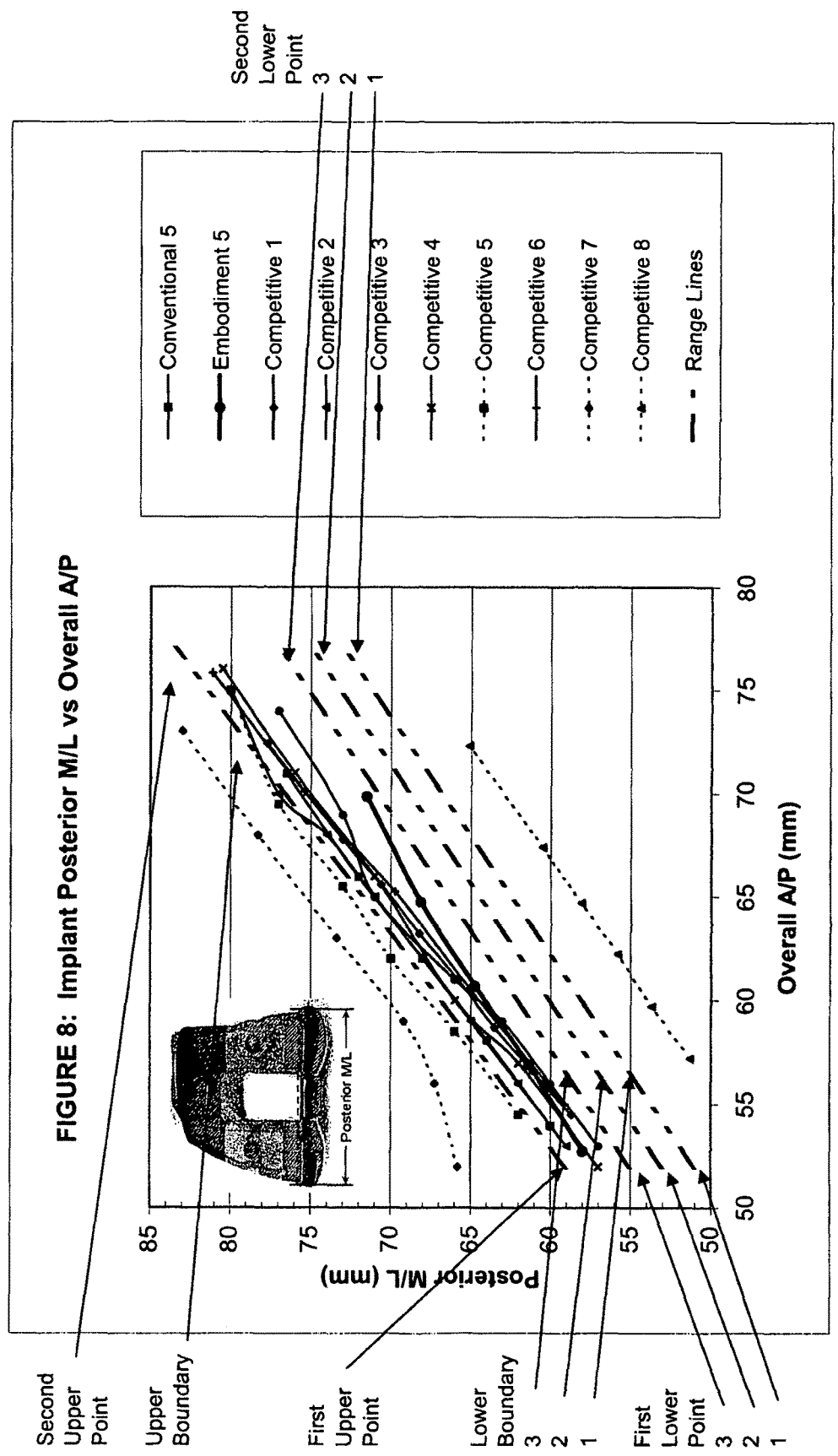

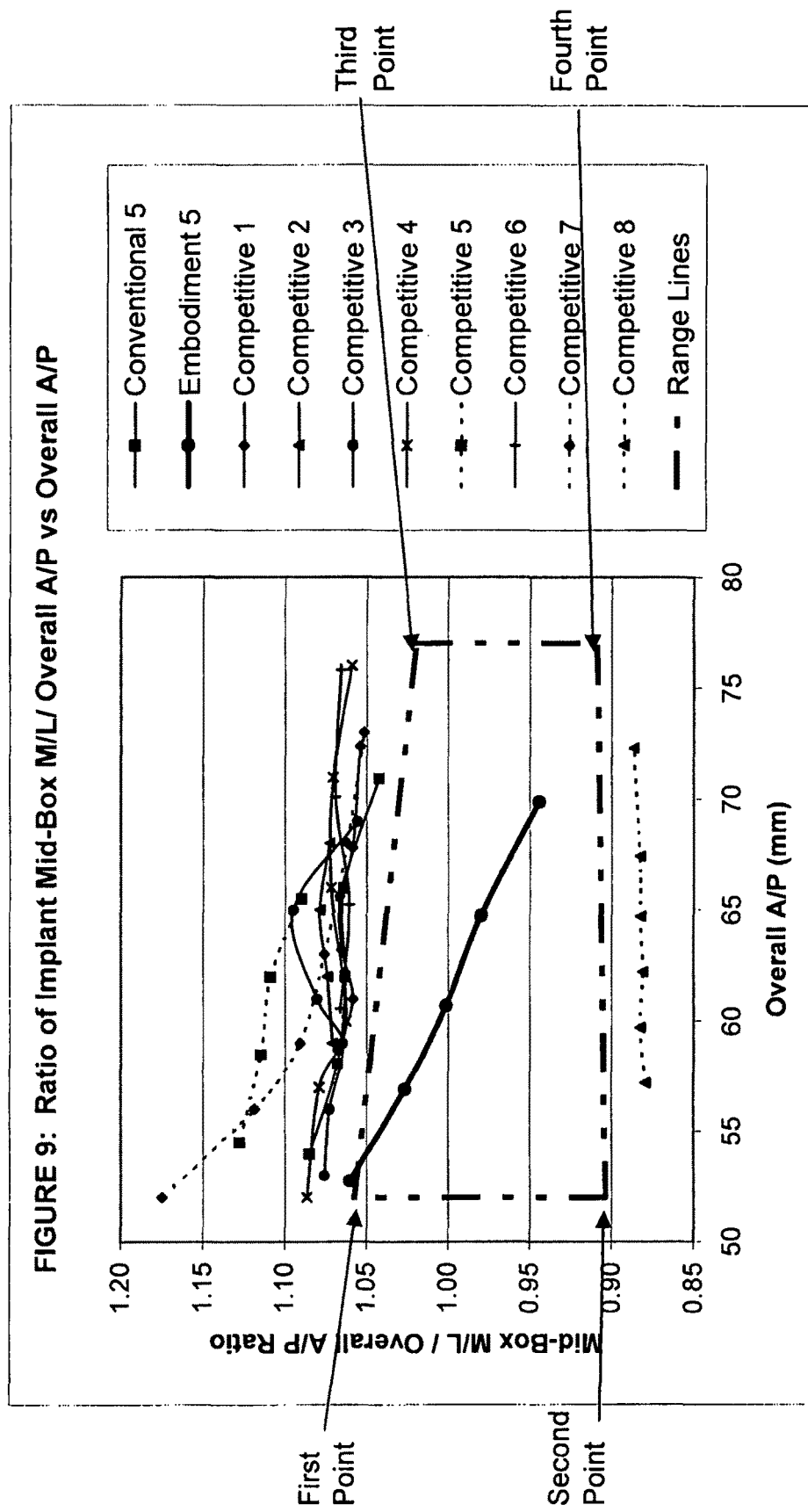

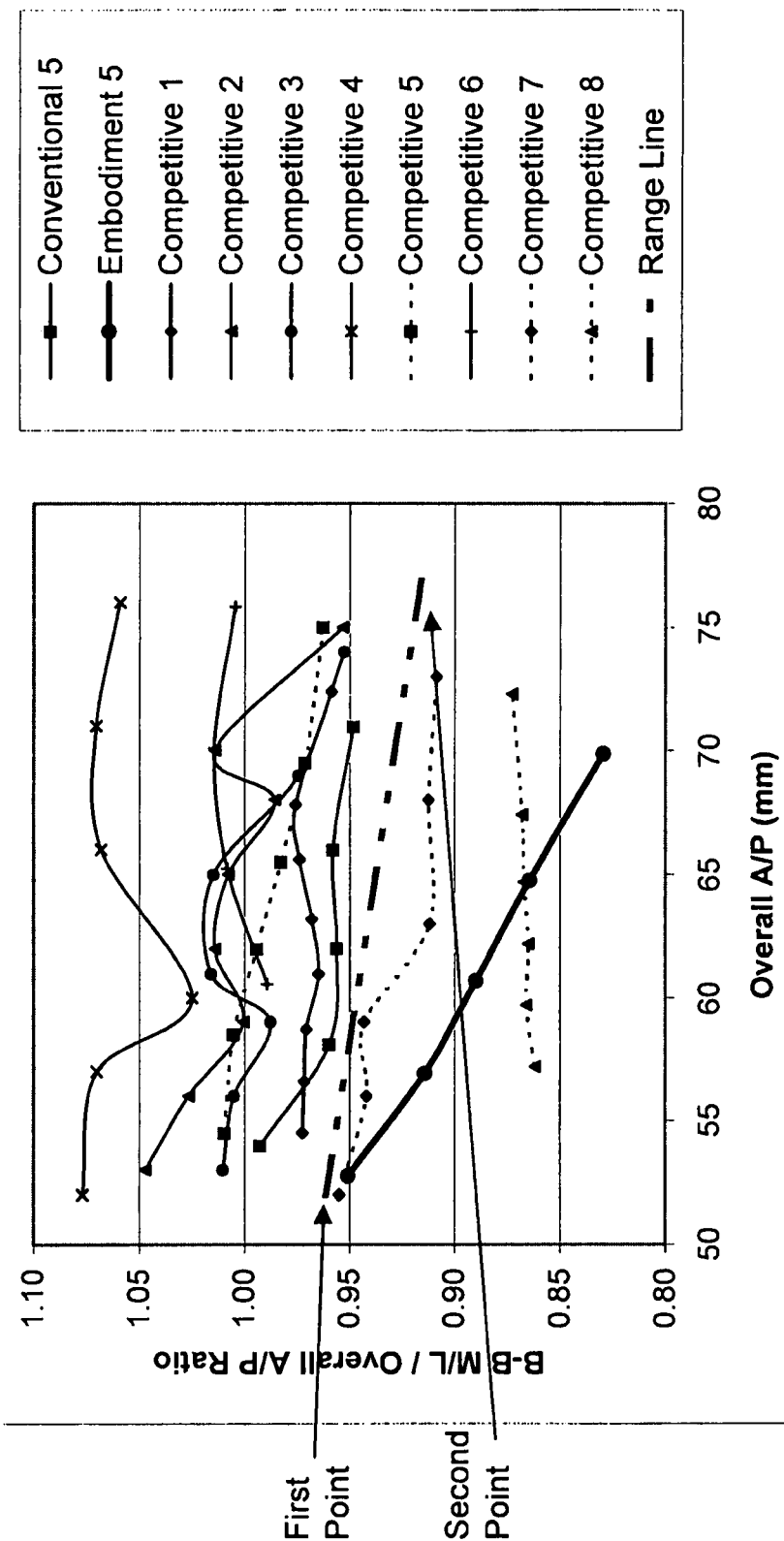

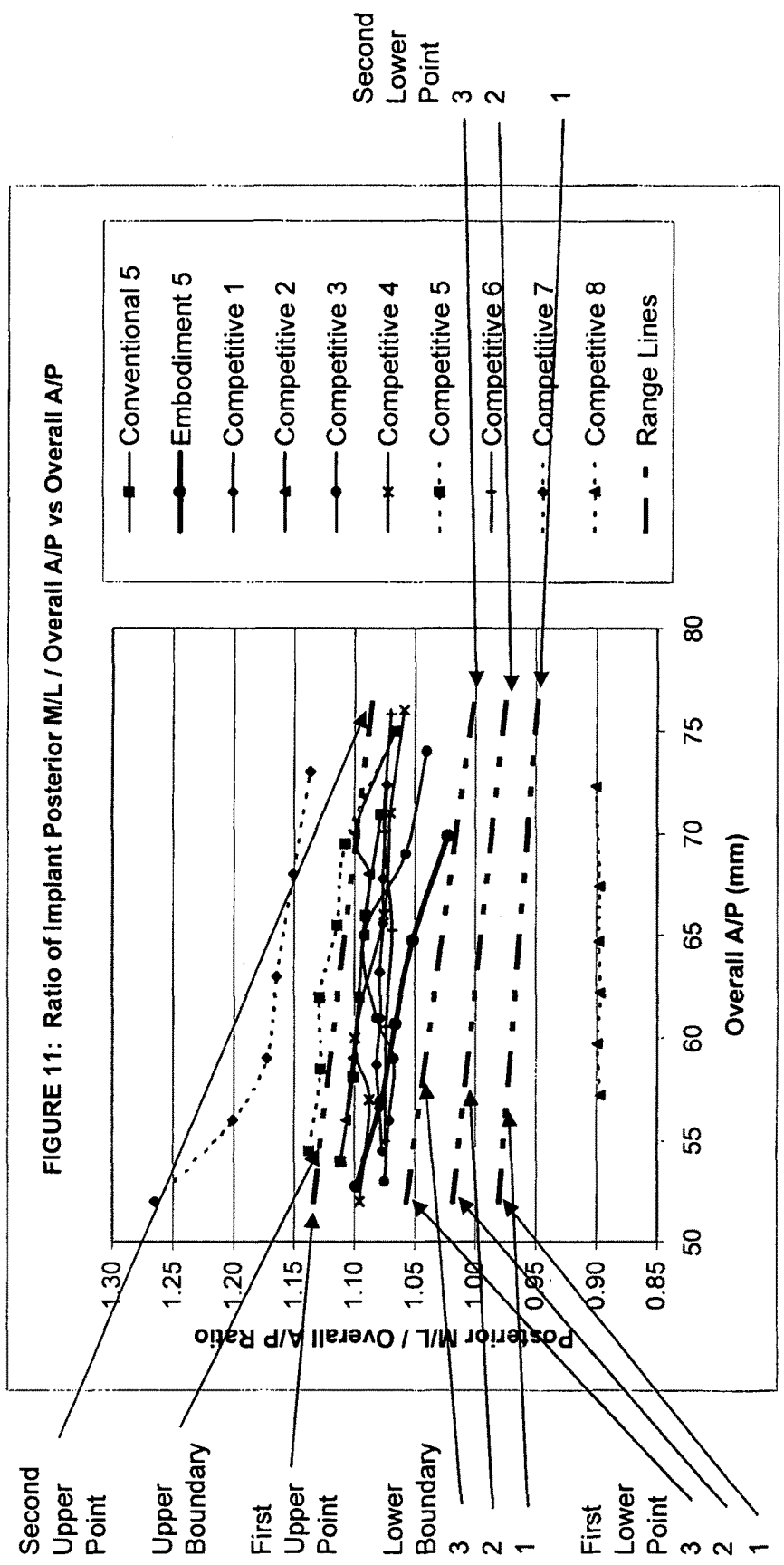

FIG_15

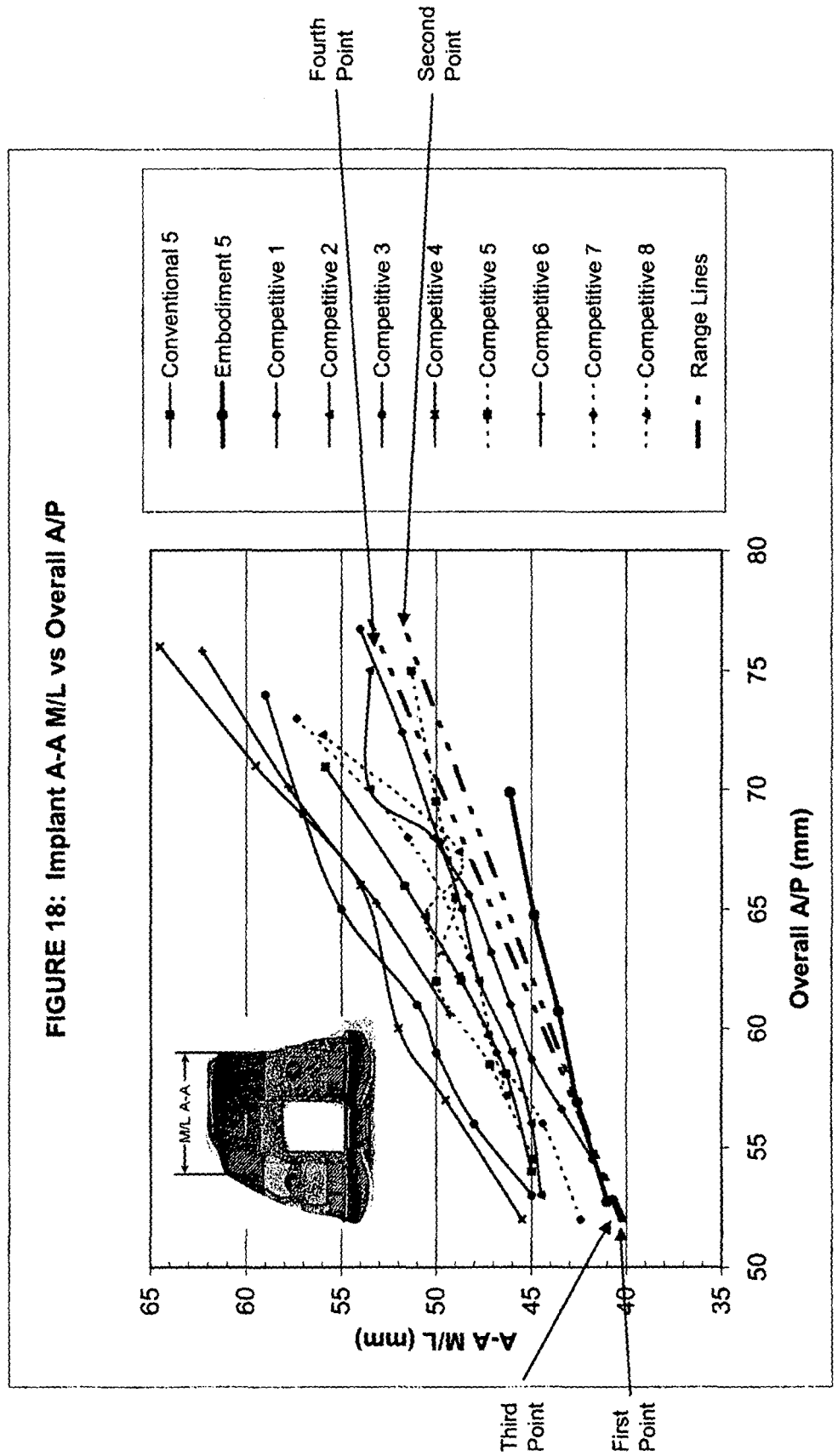

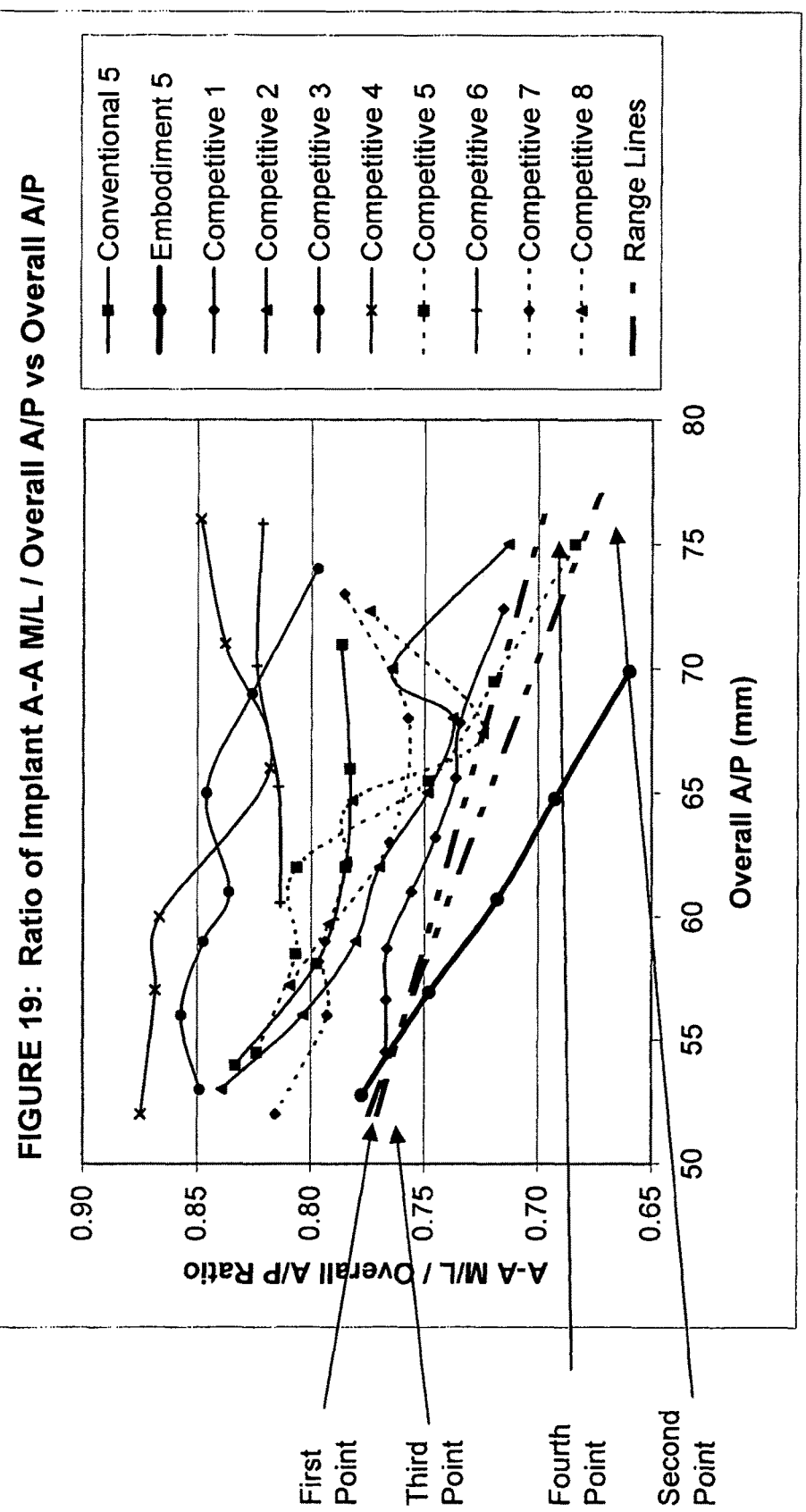

DISTAL FEMORAL KNEE PROSTHESES

CROSS REFERENCE TO RELATED APPLICATIONS

This application claims the benefit under Title 35, U.S.C. §119(e) of U.S. Provisional Patent Application Ser. No. 60/750,613, entitled Distal Femoral Knee Prostheses, filed Dec. 15, 2005, and U.S. Provisional Patent Application Ser. No. 60/805,933, entitled Distal Femoral Knee Prostheses, filed Jun. 27, 2006, the disclosures of which are each hereby expressly incorporated herein by reference.

BACKGROUND

1. Field of the Invention

The present invention relates generally to orthopedic prosthetic devices and, in particular, to distal femoral knee prostheses.

2. Description of the Related Art

Disease and trauma affecting the articular surfaces of a knee joint are commonly effectively treated by surgically replacing the articulating ends of the femur and tibia with prosthetic femoral and tibial implants or prostheses according to a procedure known as a total knee replacement ("TKR") or a total knee arthroplasty ("TKA"). The femoral and tibial implants are made of materials that exhibit a low coefficient of friction as they articulate against one another to restore normal knee function.

Although distal femoral knee prostheses are provided in a range of varying sizes and are selected by surgeons to best fit the anatomy of a particular patient, improvements in the design of distal femoral knee prostheses are desired.

SUMMARY

The present invention provides a set of distal femoral knee prostheses which are designed to be more narrow in medial/lateral ("M/L") dimensions with increasing anterior/posterior ("A/P") size than existing prostheses to more closely correspond to the physical anatomy of female patients. The prostheses are designed to have a substantially trapezoidal shape or profile when viewed distally which features a more pronounced narrowing of the M/L dimensions beginning at the posterior end of the prostheses and progressing anteriorly to the anterior end of the prostheses. Additionally, the prostheses each include a reduced profile patellar sulcus and reduced profile anterior condyles to more closely conform to the anatomy of a resected femur, and also include sulcus tracking which is optimized to conform to female anatomy.

In one form thereof, the present disclosure provides a set of distal femoral prostheses particularly adapted for female anatomy, each femoral prosthesis including a distal nonarticulating surface having an anterior end and a posterior end, including a plurality of standard aspect ratio prostheses respectively having increasingly greater overall anterior/posterior dimensions defined between points located most anteriorly and most posteriorly on each prosthesis and having increasingly greater distal taper angles defined between a lateral line connecting the anterior end and the posterior end of the distal nonarticulating surface and a medial line connecting the anterior end and the posterior end of the distal nonarticulating surface on each prosthesis; at least some of the prostheses having a distal taper angle greater than or equal to approximately 21°.

In another form thereof, the present disclosure provides a set of distal femoral prostheses particularly adapted for female anatomy, each femoral prosthesis including a distal nonarticulating surface having an anterior end and a posterior end, including a plurality of standard aspect ratio prostheses each having an overall anterior/posterior dimension defined between points located most anteriorly and most posteriorly on each prosthesis and a medial/lateral dimension defined between points located most medially and most laterally at anterior/posterior locations substantially equidistant from the anterior end of the distal nonarticulating surface and the posterior end of the distal nonarticulating surface; at least some of the prostheses having an overall anterior/posterior dimension and a medial/lateral dimension falling below a conceptual boundary defined by a line connecting a first point and a second point, the first point having an approximately 52.0 overall anterior/posterior dimension and an approximately 55.0 medial/lateral dimension, and the second point having an approximately 77.0 overall anterior/posterior dimension and an approximately 78.5 medial/lateral dimension; wherein the line is defined by the following equation: (medial/lateral dimension)=(0.94*overall anterior/posterior dimension)+6.12.

In yet another form thereof, the present disclosure provides a set of distal femoral prostheses particularly adapted for female anatomy, each femoral prosthesis including a distal nonarticulating surface having an anterior end and a posterior end, including a plurality of standard aspect ratio prostheses respectively having increasingly greater overall anterior/posterior dimensions defined between points located most anteriorly and most posteriorly on each prosthesis and respectively having increasingly greater medial/lateral dimensions defined between points located most medially and most laterally at an anterior/posterior location defined by the anterior end of the distal nonarticulating surface on each prosthesis; at least some of the prostheses having an overall anterior/posterior dimension and a medial/lateral dimension falling below a conceptual boundary defined by a line connecting a first point and a second point, the first point having an approximately 52.0 overall anterior/posterior dimension and an approximately 50.0 medial/lateral dimension, and the second point having an approximately 77.0 overall anterior/posterior dimension and an approximately 70.5 medial/lateral dimension; wherein the line is defined by the following equation: (medial/lateral dimension)=(0.82*overall anterior/posterior dimension)+7.36.

In still another form thereof, the present disclosure provides a set of distal femoral prostheses particularly adapted for female anatomy, each femoral prosthesis including a distal nonarticulating surface and an anterior nonarticulating surface, including a plurality of standard aspect ratio prostheses respectively having increasingly greater overall anterior/posterior dimensions defined between points located most anteriorly and most posteriorly on each prosthesis and respectively having increasingly greater medial/lateral dimensions defined between points located most medially and most laterally at an anterior/posterior location defined by a distal most point on the anterior nonarticulating surface on each prosthesis; at least some of the prostheses having an overall anterior/posterior dimension and a medial/lateral dimension falling below a conceptual boundary defined by a line connecting a first point and a second point, the first point having an approximately 52.0 overall anterior/posterior dimension and an approximately 40.1 medial/lateral dimension, and the second point having an approximately 77.0 overall anterior/posterior dimension and an approximately 53.5 medial/lateral dimension; wherein the line is defined by the following equation: (medial/lateral dimension)=(0.54*overall anterior/posterior dimension)+12.23.

In another form thereof, the present disclosure provides a set of distal femoral prostheses particularly adapted for female anatomy, each femoral prosthesis including a distal nonarticulating surface and an anterior nonarticulating surface, including a plurality of prostheses respectively having increasingly greater overall anterior/posterior dimensions defined between points located most anteriorly and most posteriorly on each prosthesis and respectively having increasingly greater medial/lateral dimensions defined between points located most medially and most laterally at an anterior/posterior location defined by a distal most point on the anterior nonarticulating surface on each prosthesis; at least some of the prostheses having an overall anterior/posterior dimension and a medial/lateral dimension falling below a conceptual boundary defined by a line connecting a first point and a second point, the first point having an approximately 52.0 overall anterior/posterior dimension and an approximately 40.3 medial/lateral dimension, and the second point having an approximately 77.0 overall anterior/posterior dimension and an approximately 51.8 medial/lateral dimension; wherein the line is defined by the following equation: (medial/lateral dimension)=(0.46*overall anterior/posterior dimension)+16.38.

In a still further form thereof, the present disclosure provides a set of distal femoral prostheses particularly adapted for female anatomy, each femoral prosthesis including a distal nonarticulating surface having an anterior end and a posterior end, including a plurality of prostheses each having an overall anterior/posterior dimension defined between points located most anteriorly and most posteriorly on each prosthesis and a medial/lateral dimension defined between points located most medially and most laterally at anterior/posterior locations substantially equidistant from the anterior end of the distal nonarticulating surface and the posterior end of the distal nonarticulating surface; at least some of the overall anterior/posterior dimensions and the medial/lateral dimensions falling within a conceptual boundary defined by an upper line and a lower line, the upper line connecting a first point and a third point, the lower line connecting a second point and a fourth point, the first point having an approximately 52.0 overall anterior/posterior dimension and an approximately 55.0 medial/lateral dimension, the second point having an approximately 52.0 overall anterior/posterior dimension and an approximately 47.0 medial/lateral dimension, the third point having an approximately 77.0 overall anterior/posterior dimension and an approximately 78.5 medial/lateral dimension, and the fourth point having an approximately 77.0 overall anterior/posterior dimension and an approximately 70.0 medial/lateral dimension; wherein the upper line is defined by the following equation: (medial/lateral dimension)=(0.94*overall anterior/posterior dimension)+6.12; and wherein the lower line is defined by the following equation: (medial/lateral dimension)=(0.92*overall anterior/posterior dimension)−0.84.

In yet another form thereof, the present disclosure provides a set of distal femoral prostheses particularly adapted for female anatomy, each femoral prosthesis including a distal nonarticulating surface having an anterior end and a posterior end, including a plurality of standard aspect ratio prostheses respectively having increasingly greater overall anterior/posterior dimensions defined between points located most anteriorly and most posteriorly on each prosthesis and having increasingly greater medial/lateral dimensions defined between points located most medially and most laterally at an anterior/posterior location substantially equidistant from the anterior end of the distal nonarticulating surface and the posterior end of the distal nonarticulating surface on each prosthesis; the medial/lateral dimensions of the prostheses respectively increasing at a first rate, the overall anterior/posterior dimensions respectively increasing at a second rate, the first rate and the second rate defining a ratio substantially equal to or less than 0.89.

In still another form thereof, the present disclosure provides a set of distal femoral prostheses particularly adapted for female anatomy, each femoral prosthesis including a distal nonarticulating surface having an anterior end and a posterior end, including a plurality of prostheses respectively having increasingly greater overall anterior/posterior dimensions defined between points located most anteriorly and most posteriorly on each prosthesis and having increasingly greater medial/lateral dimensions defined between points located most medially and most laterally at an anterior/posterior location substantially equidistant from the anterior end of the distal nonarticulating surface and the posterior end of the distal nonarticulating surface on each prosthesis; the medial/lateral dimensions of the prostheses respectively increasing at a first rate, the overall anterior/posterior dimensions respectively increasing at a second rate, the first rate and the second rate defining a ratio substantially equal to or less than 0.75.

In a further form thereof, the present disclosure provides a set of distal femoral prostheses particularly adapted for female anatomy, including a plurality of standard aspect ratio prostheses respectively having increasingly greater overall anterior/posterior dimensions defined between points located most anteriorly and most posteriorly on each prosthesis and having increasingly greater medial/lateral dimensions defined between points located most medially and most laterally at an anterior/posterior location defined at a location proximate the most posteriorly located point on each prosthesis; the medial/lateral dimensions of the prostheses respectively increasing at a first rate, the overall anterior/posterior dimensions respectively increasing at a second rate, the first rate and the second rate defining a ratio substantially equal to or less than 0.96.

In another form thereof, the present disclosure provides a set of distal femoral prostheses particularly adapted for female anatomy, including a plurality of prostheses respectively having increasingly greater overall anterior/posterior dimensions defined between points located most anteriorly and most posteriorly on each prosthesis and having increasingly greater medial/lateral dimensions defined between points located most medially and most laterally at an anterior/posterior location defined at a location proximate the most posteriorly located point on each prosthesis; the medial/lateral dimensions of the prostheses respectively increasing at a first rate, the overall anterior/posterior dimensions respectively increasing at a second rate, the first rate and the second rate defining a ratio substantially equal to or less than 0.84.

In still another form thereof, the present disclosure provides a set of distal femoral prostheses particularly adapted for female anatomy, each femoral prosthesis including a distal nonarticulating surface having an anterior end and a posterior end, including a plurality of standard aspect ratio prostheses respectively having increasingly greater overall anterior/posterior dimensions defined between points located most anteriorly and most posteriorly on each prosthesis and respectively having increasingly greater medial/lateral dimensions defined between points located most medially and most laterally at an anterior/posterior location defined by the anterior end of the distal nonarticulating surface on each prosthesis; the medial/lateral dimensions of the prostheses respectively increasing at a first rate, the overall anterior/posterior dimensions respectively increasing at a second rate, the first rate and the second rate defining a ratio substantially equal to or less than 0.78.

In yet another form thereof, the present disclosure provides a set of distal femoral prostheses particularly adapted for female anatomy, each femoral prosthesis including a distal nonarticulating surface having an anterior end and a posterior end, including a plurality of prostheses respectively having increasingly greater overall anterior/posterior dimensions defined between points located most anteriorly and most posteriorly on each prosthesis and respectively having increasingly greater medial/lateral dimensions defined between points located most medially and most laterally at an anterior/posterior location defined by the anterior end of the distal nonarticulating surface on each prosthesis; the medial/lateral dimensions of the prostheses respectively increasing at a first rate, the overall anterior/posterior dimensions respectively increasing at a second rate, the first rate and the second rate defining a ratio substantially equal to or less than 0.76.

In another form thereof, the present disclosure provides a set of distal femoral prostheses particularly adapted for female anatomy, each femoral prosthesis including a distal nonarticulating surface and an anterior nonarticulating surface, including a plurality of standard aspect ratio prostheses respectively having increasingly greater overall anterior/posterior dimensions defined between points located most anteriorly and most posteriorly on each prosthesis and respectively having increasingly greater medial/lateral dimensions defined between points located most medially and most laterally at an anterior/posterior location defined by a distal most point on the anterior nonarticulating surface on each prosthesis; the medial/lateral dimensions of the prostheses respectively increasing at a first rate, the overall anterior/posterior dimensions respectively increasing at a second rate, the first rate and the second rate defining a ratio substantially equal to or less than 0.44.

In a further form thereof, the present disclosure provides a set of distal femoral prostheses particularly adapted for female anatomy, each femoral prosthesis including a distal nonarticulating surface having an anterior end and a posterior end, including a plurality of prostheses respectively having increasingly greater overall anterior/posterior dimensions defined between points located most anteriorly and most posteriorly on each prosthesis and having increasingly greater distal taper angles defined between a lateral line connecting the anterior end and the posterior end of the distal nonarticulating surface and a medial line connecting the anterior end and the posterior end of the distal nonarticulating surface on each prosthesis; the distal taper angles of the prostheses respectively increasing at a first rate, the overall anterior/posterior dimensions of the prostheses respectively increasing at a second rate, the first rate and the second rate defining a ratio substantially equal to or greater than 0.22.

In still another form thereof, the present disclosure provides a set of distal femoral prostheses particularly adapted for female anatomy, each femoral prosthesis including a distal nonarticulating surface having an anterior end and a posterior end, including a plurality of prostheses respectively having increasingly greater overall anterior/posterior dimensions defined between points located most anteriorly and most posteriorly on each prosthesis and having increasingly greater distal taper angles defined between a lateral line connecting the anterior end and the posterior end of the distal nonarticulating surface and a medial line connecting the anterior end and the posterior end of the distal nonarticulating surface on each prosthesis; at least some of the overall anterior/posterior dimensions and the distal taper angles falling within a conceptual boundary defined by an upper boundary and a lower boundary, the upper boundary defined by a line connecting a first point and a third point, the lower boundary defined by a line connecting a second point and a fourth point, the first point having an approximately 52.0 overall anterior/posterior dimension and an approximately 27.0° distal taper angle, the second point having an approximately 58.0 overall anterior/posterior dimension and an approximately 22.5° distal taper angle, the third point having an approximately 77.0 overall anterior/posterior dimension and an approximately 32.0° distal taper angle, and the fourth point having an approximately 77.0 overall anterior/posterior dimension and an approximately 26.0° distal taper angle.

In yet another form thereof, the present disclosure provides a set of distal femoral prostheses particularly adapted for female anatomy, each femoral prosthesis including a distal nonarticulating surface having an anterior end and a posterior end, including a plurality of prostheses respectively having increasingly greater overall anterior/posterior dimensions defined between points located most anteriorly and most posteriorly on each prosthesis and having increasingly greater distal taper angles defined between a lateral line connecting the anterior end and the posterior end of the distal nonarticulating surface and a medial line connecting the anterior end and the posterior end of the distal nonarticulating surface on each prosthesis; at least some of the overall anterior/posterior dimensions and the distal taper angles falling within a conceptual boundary defined by an upper boundary and a lower boundary, the upper boundary defined by a line connecting a first point and a third point, the lower boundary defined by a line connecting a second point and a fourth point, the first point having an approximately 52.0 overall anterior/posterior dimension and an approximately 34.0° distal taper angle, the second point having an approximately 58.0 overall anterior/posterior dimension and an approximately 22.5° distal taper angle, the third point having an approximately 77.0 overall anterior/posterior dimension and an approximately 32.0° distal taper angle, and the fourth point having an approximately 77.0 overall anterior/posterior dimension and an approximately 26.0° distal taper angle.

In a further form thereof, the present disclosure provides a distal femoral prosthesis, including a non-articulating surface including a distal plane and an anterior non-articular surface; lateral and medial anterior condyles; a patellar sulcus defined between the condyles, the patellar sulcus having a maximum thickness between approximately 2.5 mm and 3.2 mm between an anterior most point on the sulcus and the anterior non-articular surface.

In another form thereof, the present disclosure provides a distal femoral prosthesis, including a non-articulating surface including a distal plane and an anterior non-articular surface; lateral and medial anterior condyles each defining an anterior articular surface, at least one of the condyles having a maximum thickness between approximately 4.0 mm and 6.1 mm between an anterior most point on the anterior articular surface of the condyle and the anterior non-articular surface.

In yet another form thereof, the present disclosure provides a distal femoral prosthesis, including a patellar sulcus disposed between lateral and medial anterior condyles of the prosthesis, the sulcus having an end point; a non-articulating surface having a distal plane; and a lateralization distance defined at the end point between a first line extending from an intersection of the distal plane and the sulcus and the end point, the lateralization distance greater than 5.0 mm.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 5 is a graph illustrating a representative anatomical mid-box M/L vs. A/P dimensional relationship with respect to male and female femurs of various size;

FIG. 6 is a graph of mid-box M/L vs. overall A/P for prostheses designed in accordance with the present invention as compared with several known prostheses;

FIG. 7 is a graph of anterior M/L along a dimension "B-B" vs. overall A/P for prostheses designed in accordance with the present invention as compared with several known prostheses;

FIG. 8 is a graph of posterior M/L vs. overall A/P for prostheses designed in accordance with the present invention as compared with several known prostheses;

FIG. 9 is a graph of the ratio of (mid-box M/L/overall A/P) vs. overall A/P for the prostheses of FIG. 6;

FIG. 10 is a graph of the ratio of (anterior M/L along dimension "B-B"/overall A/P) vs. overall A/P for the prostheses of FIG. 7;

FIG. 11 is a graph of the ratio of (posterior M/L/overall A/P) vs. overall A/P for the prostheses of FIG. 8;

FIG. 18 is a graph of A-A M/L vs. overall A/P for prostheses designed in accordance with the present invention as compared with several known prostheses; and FIG. 19 is a graph of the ratio of (A-A M/L/overall A/P) vs. overall A/P for the prostheses of FIG. 18.

Corresponding reference characters indicate corresponding parts throughout the several views. The exemplifications set out herein illustrate exemplary embodiments of the invention, and such exemplifications are not to be construed as limiting the scope of the invention any manner.

DETAILED DESCRIPTION

As used herein, the following directional definitions apply. Anterior and posterior mean nearer the front or nearer the rear of the body, respectively. Thus, with respect to the prostheses described herein, anterior refers to that portion of the knee that is nearer the front of the body, when the leg is in an extended position. Proximal and distal mean nearer to or further from the root of a structure, respectively. For example, the distal femur is a part of the knee joint while the proximal femur is part of the hip joint. Finally, the adjectives medial and lateral mean nearer the sagittal plane or further from the sagittal plane, respectfully. The sagittal plane is an imaginary vertical plane through the middle of the body that divides the body into right and left halves.

Distal femoral knee prostheses made in accordance with the present invention are intended to be used to restore knee joint function in patients with severe pain and disability due, for example, to Rheumatoid arthritis, osteoarthritis, traumatic arthritis polyarthritis; collagen disorders, and/or avascular necrosis of the femoral condyle; post-traumatic loss of joint configuration, particularly when there is patellofemoral erosion, dysfunction or prior patellectomy; moderate valgus, varus, flexion deformities, or other conditions.

Figure 1:
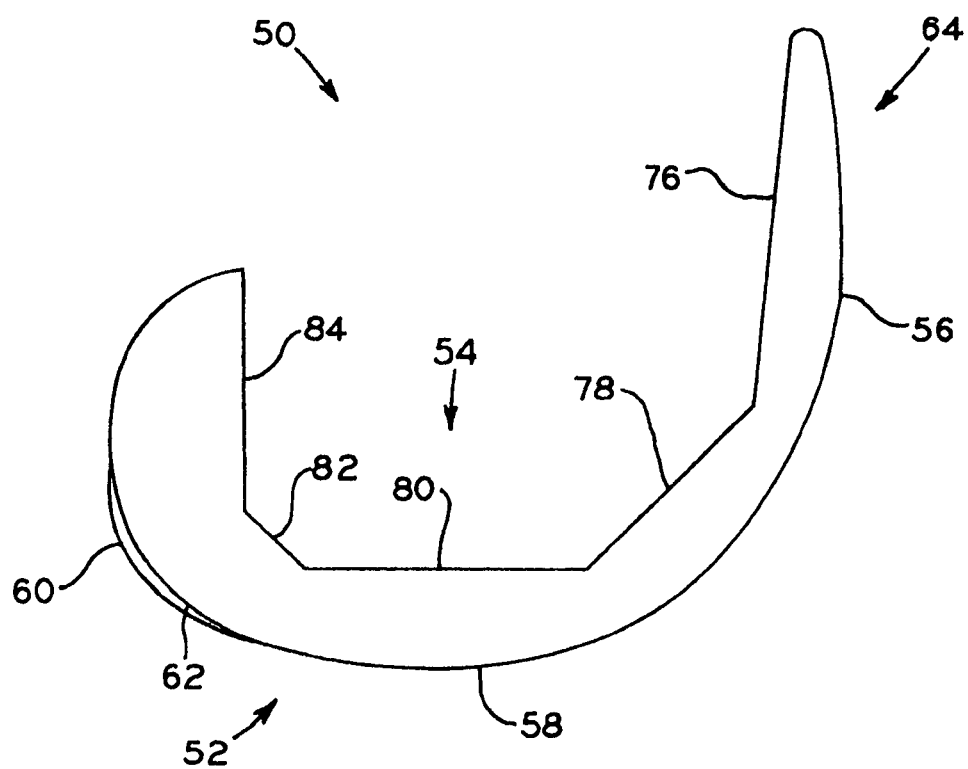
FIG. 1 is a side view of an exemplary distal femoral prosthesis in accordance with the present invention.
Figure 3:
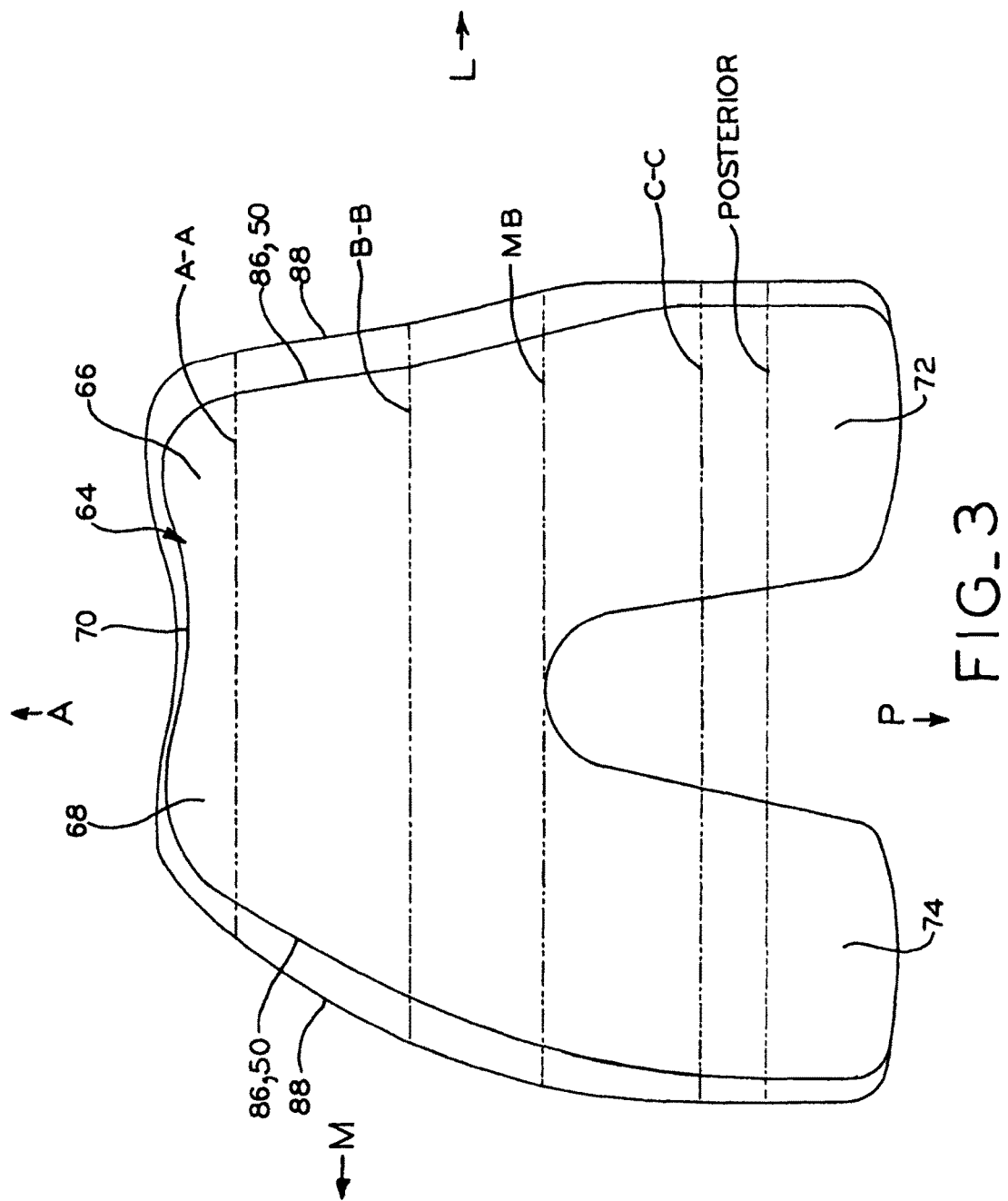
FIG. 3 is a distal view of the prosthesis of FIG. 2, viewed along line 3-3 of FIG. 2 and shown superimposed on a known prosthesis.
Figure 4:
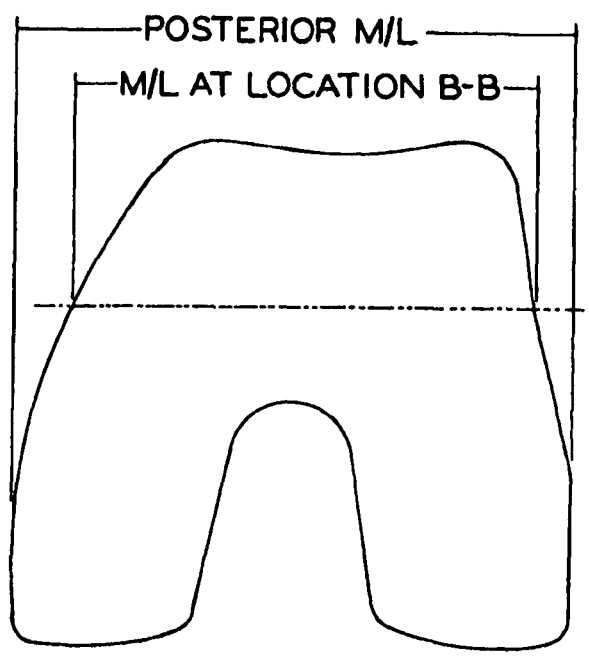
FIG. 4 further illustrates the anatomical M/L vs. A/P dimensional relationship of the prosthesis of FIG. 3 at dimension "B-B"

Referring initially to FIG. 1, a distal femoral prosthesis 50 for a TKR/TKA according to one embodiment of the present invention is shown, and generally includes an external articulating surface 52 and a bone contacting non-articulating internal surface 54. Articulating surface 52 includes an anterior articulating surface 56, a distal articulating surface 58, a lateral posterior condylar articulating surface 60, and a medial posterior condylar articulating surface 62. Prosthesis 50 may be made of any biocompatible material having the mechanical properties necessary to function as a human knee distal femoral prosthesis. Preferably, prosthesis 50 is made of titanium, titanium alloy, cobalt chrome alloy, stainless steel, or a ceramic. Referring additionally to FIG. 3, prosthesis 50 further includes patellar flange 64 including lateral and medial anterior condyles 66 and 68, respectively, as well as patellar sulcus 70 disposed between lateral and medial anterior condyles 66 and 68. Prosthesis also includes lateral and medial posterior condyles 72 and 74, respectively.

Referring to FIG. 1, the internal non-articulating portion 54 of prosthesis 50 is adapted to receive a resected distal femur. The surgical cuts made to the distal femur can be made by any means, in any sequence and in any configuration known to those of skill in the art of knee arthroplasty. Exemplary cut guides and processes for resecting the distal femur are shown and described in U.S. patent application Ser. No. 11/151,062, entitled ADJUSTABLE CUT GUIDE, filed on Jun. 13, 2005 and U.S. patent application Ser. No. 11/154,774, entitled MULTI-POSITIONABLE CUT GUIDE, filed on Jun. 16, 2005, assigned to the assignee of the present invention, the disclosures of which are expressly incorporated herein by reference.

In a preferred embodiment, prosthesis 50 comprises a plurality of chamfer surfaces corresponding to a plurality of chamfer surfaces or "box cuts" made in the distal femur. Non-articular surface 54 may comprise a porous metal surface or any surface likely to promote the growth of bone therein. Non-articular surface 54 of prosthesis 50 preferably comprises anterior non-articular surface 76, distal anterior non-articular surface 78, distal non-articular surface 80, two distal posterior non-articular surfaces 82, and two posterior non-articular surfaces 84.

Distal non-articular surface 80 is generally flat and adapted to receive the distal-most surface of the resected femur. Distal non-articular surface 80 comprises an anterior end and a posterior end. The anterior end of distal non-articular surface 80 abuts one end of distal anterior non-articular surface 78, which surface 78 also includes an anterior end and a posterior end. Surface 78 extends from surface 80 anteriorly and superiorly such that an obtuse angle is formed between surfaces 78 and 80. Anterior non-articular surface 76 extends superiorly from the anterior end of surface 78.

The posterior end of distal non-articular surface 80 abuts one end of each distal posterior non-articular surface 82, which surfaces 82 also include an anterior end and a posterior end. Surfaces 82 extend from surface 80 posteriorly and superiorly such that an obtuse angle is formed between surfaces 82 and 80. Posterior non-articular surfaces 84 extend superiorly from the posterior ends of surfaces 82, respectively.

As discussed in detail below, for many patients, particularly female patients, it is desirable to construct a set of prostheses 50 of varying size wherein the medial/lateral ("M/L") width dimensions of the prostheses correspond more closely to the actual anatomical M/L width dimensions of the female femur and articulating surfaces. As described below, prostheses 50 addresses this concern by offering the surgeon a set of narrower prostheses in the M/L dimensions for a given set of anterior/posterior ("A/P") prosthesis sizes which will allow the surgeon to use a prosthesis with both a correct A/P size and more accurate and optimized M/L dimensions to provide optimal prosthesis sizing and joint kinematics as compared to conventional prostheses.

Figure 2:
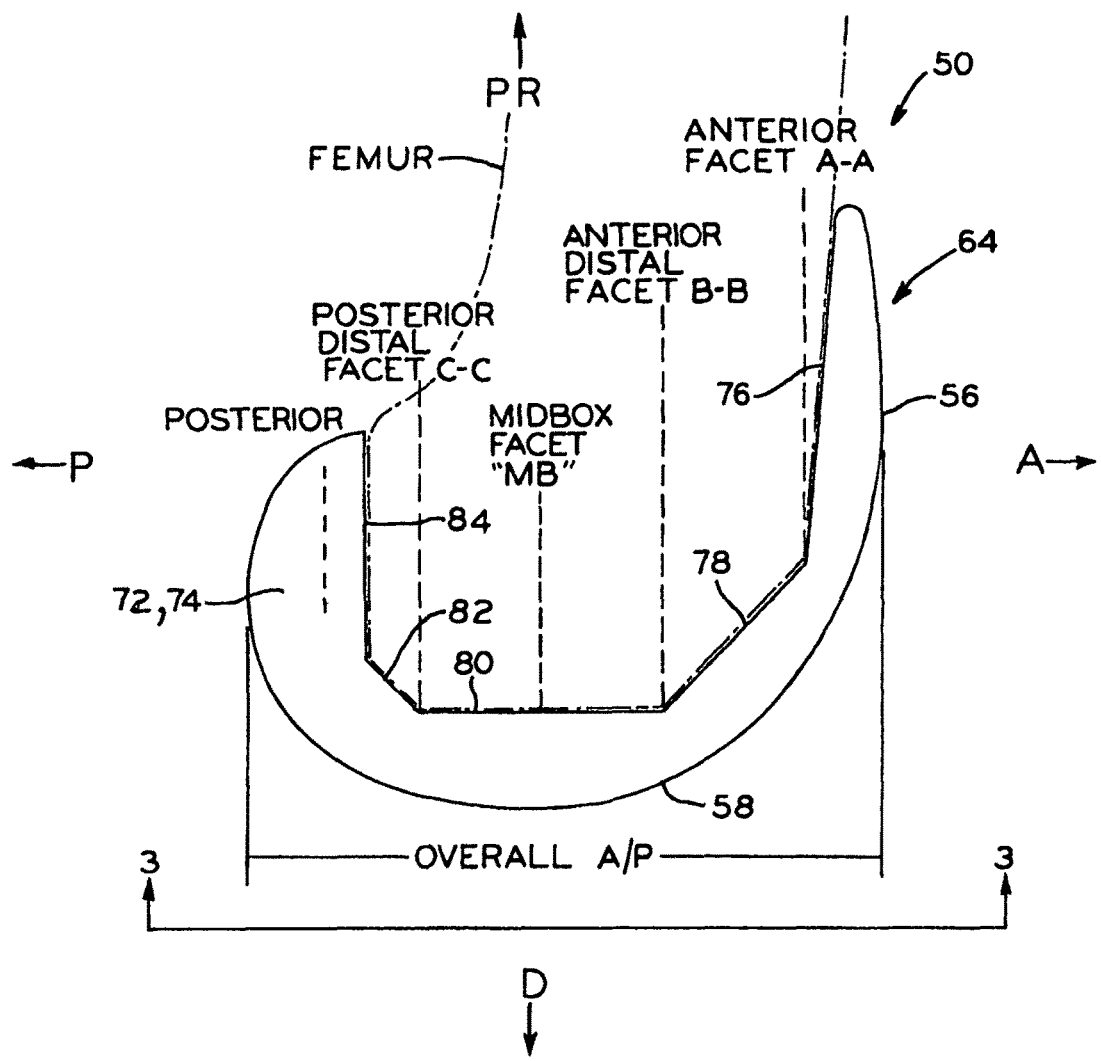
FIG. 2 is another side view of the prosthesis of FIG. 1, illustrating certain dimensions thereof.

In FIG. 3, the profile 86 of prosthesis 50 is superimposed upon profile 88 of a known prosthesis. As described in detail below, prosthesis 50 has a unique, substantially trapezoidal shape or profile 86 when viewed distally with a more pronounced narrowing of the M/L dimensions as compared to the shape or profile 88 of a known prosthesis starting, with reference to the resected femur, at the posterior distal facet and progressing anteriorly to the anterior distal facet. Referring to FIGS. 2 and 3, prosthesis 50 is shown and is characterized below with reference to the following directions: anterior "A", posterior "P", distal "D", proximal "PR", medial "M" and lateral "L", as well as the following dimensions. Dimension "Posterior" is the M/L width at the widest point across the posterior condyles 72, 74 of prosthesis 50. Dimension "C-C" is the M/L width at the junction of the posterior distal facet and the distal plane, i.e., the M/L width along the intersection between distal non-articular surface 80 and distal posterior non-articular surfaces 82. Dimension "B-B" is the M/L width at the junction of the distal plane and the distal anterior facet, i.e., the M/L width along the intersection between distal non-articular surface 80 and distal anterior non-articular surface 78. Dimension "A-A" is the M/L width at the junction of the distal anterior facet and the posterior side of the anterior flange, i.e., the M/L width along the intersection of distal anterior non-articular surface 78 and anterior non-articular surface 76. Dimension "MB" is the M/L width at a "mid-box" point of prosthesis 50, i.e., along a line located on distal non-articular surface 80 substantially midway between Dimension C-C and Dimension B-B.

Figure 5A:
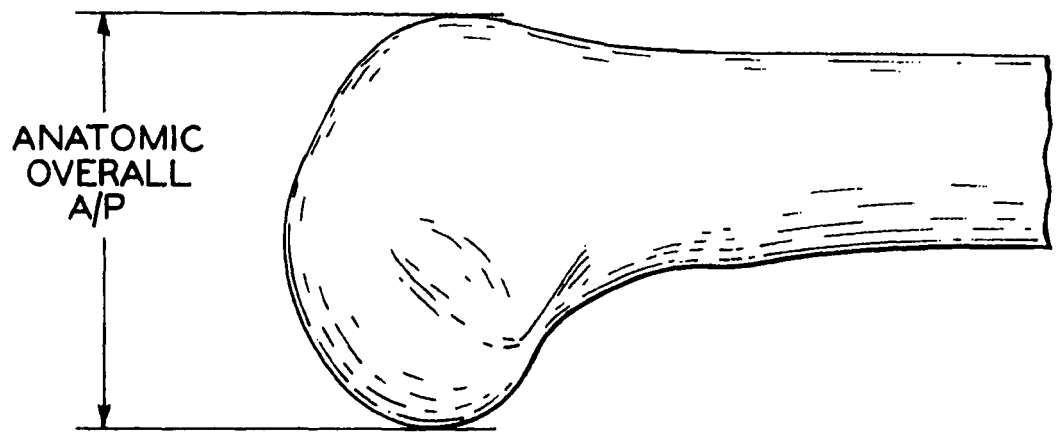
FIG. 5A is a view of an anatomic overall A/P dimension for a representative femur.
Figure 5B:
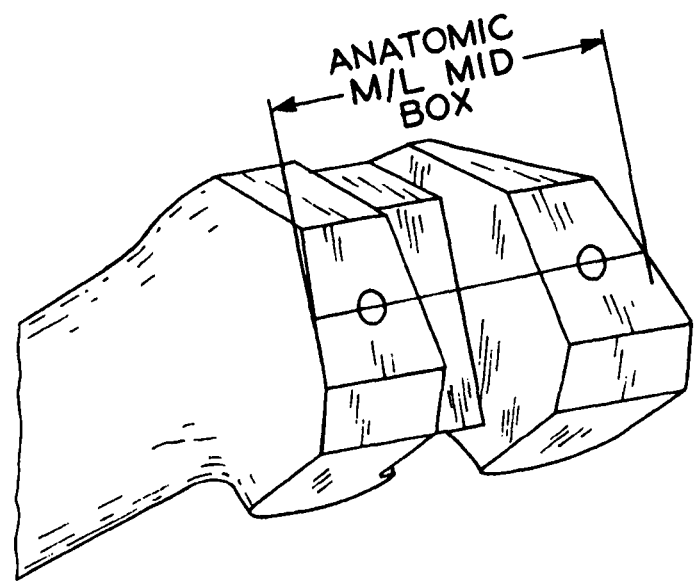
FIG. 5B is a view of an anatomic mid-box M/L dimension for a representative femur.

As described below, the profiles of a set of prostheses 50 can also be described in terms of an increasing narrowing of the M/L dimensions relative to known prostheses on a per size basis. It has been observed that, for given female femurs, for example, the M/L dimensions are sometimes smaller than those of known prostheses of the proper A/P dimension. This discrepancy is small on the smaller A/P size prostheses and increases as the A/P size increases. For example, referring to FIG. 5, a representative mid-box M/L vs. A/P dimensional relationship with respect to the actual human anatomy of distal femurs for males and females is shown. Representative female data is generally grouped together at lower values of mid-box M/L and representative male data is generally grouped together at higher values of mid-box M/L. Best fit lines for female and male data have been included on FIG. 5 to show the general trend of representative mid-box M/L dimensions. As may be seen from FIG. 5, there exists a clear distinction between the representative M/L dimension vs. the A/P dimension for a female distal femur as compared to a male distal femur. FIGS. 5A and 5B show exemplary anatomic overall A/P and mid-box M/L dimensions for a representative femur.

In FIG. 2, the overall A/P ("Overall A/P") dimension is the distance between two lines perpendicular to distal non-articular surface 80 that pass through the most posterior point on the posterior face of exterior articulating surface 58 and through the most anterior point on the anterior face of exterior articulating surface 58, respectively. FIG. 2 also shows a dashed outline of a resected femur with prosthesis 50 positioned thereon.

As an exemplary comparison, the dimensions "Posterior", "B-B", "A-A", and "Overall A/P" and the ratios of these values for conventional prostheses ("Conventional 1", including five increasing sizes C through G) are compared with corresponding dimensions and ratios of a set of prostheses designed in accordance with the present invention ("Embodiment 1", including five increasing sizes C through G). These values are presented in Table 1 below. Unless otherwise indicated, all numerical dimensional values presented herein are in millimeters ("mm").

TABLE 1

| SIZE | Overall A/P | "Post." | "B-B" | "A-A" | Overall A/P | "Post." | "B-B" | "A-A" |
|---|---|---|---|---|---|---|---|---|
| | Embodiment 1 | | | | Conventional 1 | | | |
| C | 52.2 | 58.0 | 49.6 | 41.1 | 53.5 | 60.0 | 53.6 | 45.1 |
| D | 56.3 | 61.3 | 51.5 | 42.6 | 57.6 | 64.0 | 55.8 | 46.5 |
| E | 60.2 | 64.5 | 53.5 | 43.7 | 61.5 | 68.0 | 59.3 | 49.1 |
| F | 64.2 | 67.9 | 55.4 | 45.0 | 65.4 | 72.0 | 63.2 | 52.0 |
| G | 69.2 | 71.0 | 57.3 | 46.3 | 70.4 | 76.5 | 67.3 | 56.2 |

TABLE 1-continued

| SIZE | Overall A/P | "Post." | "B-B" | "A-A" | Overall A/P | "Post." | "B-B" | "A-A" |
|---|---|---|---|---|---|---|---|---|
| | Embodiment 1 - M/L/"Overall A/P" RATIOS | | | | Conventional 1 - M/L/"Overall A/P" RATIOS | | | |
| C | 52.2 | 1.11 | 0.95 | 0.79 | 53.5 | 1.12 | 1.00 | 0.84 |
| D | 56.3 | 1.09 | 0.92 | 0.76 | 57.6 | 1.11 | 0.97 | 0.81 |
| E | 60.2 | 1.07 | 0.89 | 0.73 | 61.5 | 1.11 | 0.96 | 0.80 |
| F | 64.2 | 1.06 | 0.86 | 0.70 | 65.4 | 1.10 | 0.97 | 0.79 |
| G | 69.2 | 1.03 | 0.83 | 0.67 | 70.4 | 1.09 | 0.96 | 0.80 |

Table 2 below sets forth the results of a first order equation fit to data sets for several sets of prostheses including Conventional 1, Conventional 2 (which is similar to Conventional 1), Embodiment 1, Embodiment 2 (which is similar to Embodiment 1), as well as five other sets of known competitive prostheses, designated Competitive 1, Competitive 2, Competitive 3, Competitive 4, and Competitive 5. The data sets include Posterior M/L vs. Overall A/P and the Ratio (Posterior M/L vs. Overall A/P) vs. Overall A/P.

TABLE 2

| | Posterior M/L vs. Overall A/P Best fit regression line | | Ratio (Posterior M/L/Overall A/P) vs. Overall A/P Best fit regression line | |
|---|---|---|---|---|
| | Equation | Slope | Equation | Slope |
| Conventional 1 | y = 0.9811x + 7.595 | 0.9811 | y = −0.002x + 1.2277 | −0.0020 |
| Conventional 2 | y = 0.9878x + 6.0634 | 0.9878 | y = −0.0015x + 1.1798 | −0.0015 |
| Embodiment 1 | y = 0.8036x + 16.228 | 0.8036 | y = −0.0044x + 1.3431 | −0.0044 |
| Embodiment 2 | y = 0.809x + 14.987 | 0.8090 | y = −0.0039x + 1.2965 | −0.0039 |
| Competitive 1 | y = 0.9411x + 7.1008 | 0.9411 | y = −0.0016x + 1.1565 | −0.0016 |
| Competitive 2 | y = 0.987x + 6.8225 | 0.9870 | y = −0.0017x + 1.2015 | −0.0017 |
| Competitive 3 | y = 0.976x + 5.7825 | 0.9760 | y = −0.0013x + 1.1521 | −0.0013 |
| Competitive 4 | y = 0.9757x + 6.6279 | 0.9757 | y = −0.0016x + 1.1836 | −0.0016 |
| Competitive 5 | y = 0.9336x + 11.318 | 0.9336 | y = −0.0031x + 1.3111 | −0.0031 |

From the data in Table 2, it may be seen that there is a difference in the slopes of the sets of prostheses of Embodiments 1 and 2 as compared to the slopes of the sets of the known prostheses. In particular, it may be seen from the data in Table 2 that the sets of prostheses of Embodiments 1 and 2 have a narrowing posterior M/L dimension with increasing A/P size, as indicated by slopes less than 0.93, for example, as opposed to a substantially parallel or one-to-one relationship between the posterior M/L dimension and the A/P dimension with increasing A/P size as in the sets of known prostheses, as indicated by slopes of 0.93 and above. Thus, in the sets of known prostheses, the posterior M/L dimension and the A/P dimension increase at substantially the same rate with increasing A/P size. Also, the slope of the ratio (posterior M/L/overall A/P) vs. overall A/P is less than −0.0032 for the sets of prostheses of Embodiments 1 and 2 while the corresponding slope for the known sets of prostheses is greater than −0.0032, indicating that the sets of prostheses of Embodiments 1 and 2 have an increasingly more pronounced narrowing of the posterior M/L dimension with increasing A/P size. In this manner, the sets of prostheses designed in accordance with the present invention offer a surgeon a unique combination of implant posterior M/L widths with varying A/P size for an overall system or set of prostheses, wherein such sets of prostheses are more anatomically optimized for the female anatomy as compared with the sets of known prostheses.

Table 3 below sets forth the results of a first order equation fit to data sets for several sets of prostheses including Conventional 1, Conventional 2 (which is similar to Conventional 1), Embodiment 1, Embodiment 2 (which is similar to Embodiment 1), as well as five other sets of known competitive prostheses, designated Competitive 1, Competitive 2, Competitive 3, Competitive 4, and Competitive 5. The data sets include B-B M/L vs. Overall A/P and the Ratio (B-B M/L vs. Overall A/P) vs. Overall A/P.

TABLE 3

| | Anterior M/L "B-B" vs. Overall A/P Best fit regression line | | Ratio (Anterior M/L "B-B"/Overall A/P) vs. Overall A/P Best fit regression line | |
|---|---|---|---|---|
| | Equation | Slope | Equation | Slope |
| Conventional 1 | y = 0.834x + 8.3768 | 0.8340 | y = −0.0023x + 1.112 | −0.0023 |
| Conventional 2 | y = 0.8432x + 6.9003 | 0.8432 | y = −0.0018x + 1.0681 | −0.0018 |
| Embodiment 1 | y = 0.4626x + 25.012 | 0.4626 | y = −0.0071x + 1.3173 | −0.0071 |
| Embodiment 2 | y = 0.4626x + 25.012 | 0.4626 | y = −0.0066x + 1.2797 | −0.0066 |
| Competitive 1 | y = 0.9062x + 3.2306 | 0.9062 | y = −0.0007x + 1.0017 | −0.0007 |

TABLE 3-continued

| | Anterior M/L "B-B" vs. Overall A/P Best fit regression line | | Ratio (Anterior M/L "B-B"/Overall A/P) vs. Overall A/P Best fit regression line | |
|---|---|---|---|---|
| | Equation | Slope | Equation | Slope |
| Competitive 2 | y = 0.8057x + 12.588 | 0.8057 | y = −0.0031x + 1.2033 | −0.0031 |
| Competitive 3 | y = 0.893x + 5.5381 | 0.8930 | y = −0.0012x + 1.0578 | −0.0012 |
| Competitive 4 | y = 1.0588x + 0.1731 | 1.0588 | y = −0.0001x + 1.0697 | −0.0001 |
| Competitive 5 | y = 0.7937x + 12.218 | 0.7937 | y = −0.0036x + 1.217 | −0.0036 |

From the data in Table 3, it may be seen that there is a significant difference in slope for the sets of prostheses of Embodiments 1 and 2 as compared with the slopes of the known sets of prostheses. The magnitudes of the anterior M/L "B-B" values for a given A/P dimension are more pronounced, i.e., the variance in width at dimension B-B, namely, an anterior width, over various A/P sizes between the sets of prostheses of Embodiments 1 and 2 and the known sets of prostheses is more dramatically pronounced. Specifically, sets of prostheses of Embodiments 1 and 2 have a narrowing anterior M/L dimension with increasing A/P size, as indicated by slopes less than 0.78, for example, as opposed to a substantially parallel or one-to-one relationship between the anterior M/L dimension and the A/P dimension with increasing A/P size as in the sets of known prostheses, as indicated by slopes of 0.78 and above. Thus, in the sets of known prostheses, the anterior M/L dimension and the A/P dimension increase at substantially the same rate with increasing A/P size. Also, the slope of the ratio (anterior M/L "B-B"/overall A/P) vs. overall A/P is greater than −0.0038 for the sets of prostheses of Embodiments 1 and 2, while the corresponding slope for the known sets of prostheses is less than −0.0038, indicating that the sets of prostheses of Embodiments 1 and 2 have increasingly more pronounced narrowing of the anterior M/L "B-B" dimension with increasing A/P size. In this manner, the prostheses designed in accordance with the present invention offer a surgeon a unique combination of implant M/L widths as an overall system of prostheses, wherein such sets of prostheses are more anatomically optimized for the female anatomy as compared with the sets of known prostheses.

As another exemplary comparison, the dimensions "Posterior", "MB", "B-B", and "Overall A/P" for conventional prostheses ("Conventional 3", "Conventional 4", and "Conventional 5" including five increasing sizes C through G) are compared with corresponding dimensions of a set of prostheses designed in accordance with the present invention ("Embodiment 3", "Embodiment 4", and "Embodiment 5" including five increasing sizes C through G). In one embodiment, the values for Conventional 5 and Embodiment 5 may be average values of Conventionals 3 and 4 and Embodiments 3 and 4, respectively. These values are presented in Table 4 below.

TABLE 4

| SIZE | Overall A/P | Posterior | MB | B-B | Overall A/P | Posterior | MB | B-B |
|---|---|---|---|---|---|---|---|---|
| | Embodiment 4 | | | | Conventional 4 | | | |
| C | 53.3 | 58.0 | 55.9 | 50.2 | 54.4 | 60.0 | 58.6 | 53.6 |
| D | 57.5 | 61.4 | 58.4 | 52.0 | 58.6 | 64.0 | 62.1 | 55.8 |
| E | 61.2 | 64.7 | 60.8 | 54.0 | 62.5 | 68.0 | 65.9 | 59.3 |
| F | 65.3 | 68.1 | 63.5 | 56.0 | 66.5 | 72.0 | 70.2 | 63.2 |
| G | 70.4 | 71.5 | 66.0 | 58.0 | 71.5 | 76.5 | 74.0 | 67.3 |
| | Embodiment 3 | | | | Conventional 3 | | | |
| C | 52.3 | 58.0 | 55.9 | 50.2 | 53.5 | 60.0 | 58.6 | 53.6 |
| D | 56.4 | 61.4 | 58.4 | 52.0 | 57.6 | 64.0 | 62.0 | 55.7 |
| E | 60.2 | 64.7 | 60.8 | 54.0 | 61.5 | 68.0 | 65.9 | 59.3 |
| F | 64.2 | 68.1 | 63.5 | 56.0 | 65.5 | 72.0 | 70.2 | 63.2 |
| G | 69.4 | 71.5 | 66.0 | 58.0 | 70.5 | 76.5 | 74.0 | 67.2 |
| | Embodiment 5 | | | | Conventional 5 | | | |
| C | 52.8 | 58.0 | 55.9 | 50.2 | 54.0 | 60.0 | 58.6 | 53.6 |
| D | 56.9 | 61.4 | 58.4 | 52.0 | 58.1 | 64.0 | 62.0 | 55.8 |
| E | 60.7 | 64.7 | 60.8 | 54.0 | 62.0 | 68.0 | 65.9 | 59.3 |
| F | 64.8 | 68.1 | 63.5 | 56.0 | 66.0 | 72.0 | 70.2 | 63.2 |
| G | 69.9 | 71.5 | 66.0 | 58.0 | 71.0 | 76.5 | 74.0 | 67.3 |

FIG. 6 is a graph of the dimension mid-box M/L vs. overall A/P for the following sets of prostheses, each in increasing sizes C through G: Conventional 5, Embodiment 5, as well as eight other sets of known competitive prostheses, designated Competitive 1, Competitive 2, Competitive 3, Competitive 4, Competitive 5, Competitive 6, Competitive 7, and Competitive 8.

FIG. 7 is a graph of the dimension B-B M/L vs. overall A/P for the following sets of prostheses, each in increasing sizes C through G: Conventional 5, Embodiment 5, as well as eight other sets of known competitive prostheses, designated Competitive 1, Competitive 2, Competitive 3, Competitive 4, Competitive 5, Competitive 6, Competitive 7, and Competitive 8.

FIG. 8 is a graph of the dimension Posterior M/L vs. overall A/P for the following sets of prostheses, each in increasing sizes C through G: Conventional 5, Embodiment 5, as well as eight other sets of known competitive prostheses, designated Competitive 1, Competitive 2, Competitive 3, Competitive 4, Competitive 5, Competitive 6, Competitive 7, and Competitive 8.

Table 5 below sets forth the results of a first order equation fit to each of the data sets shown in FIGS. 6, 7, and 8 as well as for the data sets of Embodiments 3 and 4 and Conventional 3 and 4 in Table 4.

TABLE 5

| Implant | Posterior M/L vs. Overall A/P Best Fit Regression Line | | Mid-box M/L vs. Overall A/P Best Fit Regression Line | | B-B M/L vs. Overall A/P Best Fit Regression Line | |
|---|---|---|---|---|---|---|
| | Slope | y-Intercept | Slope | y-Intercept | Slope | y-Intercept |
| Conventional 3 | 0.98 | 7.53 | 0.93 | 8.63 | 0.83 | 8.35 |
| Conventional 4 | 0.98 | 6.82 | 0.93 | 8.02 | 0.83 | 7.66 |
| Conventional 5 | 0.98 | 7.17 | 0.93 | 8.32 | 0.83 | 8.01 |
| Embodiment 3 | 0.80 | 16.31 | 0.60 | 24.89 | 0.46 | 26.02 |
| Embodiment 4 | 0.80 | 15.51 | 0.60 | 24.30 | 0.46 | 25.55 |
| Embodiment 5 | 0.80 | 15.91 | 0.60 | 24.59 | 0.46 | 25.79 |
| Competitive 1 | 1.06 | 1.27 | 1.01 | 3.36 | 0.94 | 1.61 |
| Competitive 2 | 0.99 | 6.82 | 1.09 | −1.10 | 0.80 | 12.80 |
| Competitive 3 | 0.98 | 5.78 | 0.91 | 11.72 | 0.83 | 10.13 |
| Competitive 4 | 0.98 | 6.63 | 1.02 | 3.40 | 1.06 | 0.17 |
| Competitive 5 | 0.90 | 13.67 | 0.91 | 11.72 | 0.82 | 10.34 |
| Competitive 6 | 1.06 | 0.61 | 1.08 | −0.70 | 1.06 | −4.03 |
| Competitive 7 | 0.86 | 19.80 | 0.77 | 19.86 | 0.78 | 9.00 |
| Competitive 8 | 0.91 | −0.64 | 0.91 | −1.64 | 0.91 | −2.64 |

From the data in Table 5, it may be seen that there is a difference in the slopes of the sets of prostheses of Embodiments 3, 4, and 5 as compared to the slopes of the sets of the known prostheses. In particular, it may be seen from the data in Table 5 that the sets of prostheses of Embodiments 3, 4, and 5 have a narrowing posterior M/L dimension with increasing A/P size, as indicated by slopes less than approximately 0.85, for example, as opposed to a substantially parallel or one-to-one relationship between the posterior M/L dimension and the A/P dimension with increasing A/P size as in the sets of known prostheses, as indicated by slopes of 0.86 and above. In exemplary embodiments, the slope of posterior M/L dimension with increasing A/P size for prostheses 50 may be as small as approximately 0.50, 0.55, 0.60, or 0.65 or as large as approximately 0.85, 0.84, 0.83, 0.81, 0.80, 0.75, or 0.70. In an exemplary embodiment, the slope of posterior M/L dimension with increasing A/P size for prostheses 50 is approximately 0.80. Thus, the posterior M/L dimension for prostheses 50 increases at a lesser rate than the corresponding overall A/P dimension. In contrast, in the sets of known prostheses, the posterior M/L dimension and the A/P dimension increase at substantially the same rate with increasing A/P size. In this manner, the sets of prostheses designed in accordance with the present invention offer a surgeon a unique combination of implant posterior M/L widths with varying A/P size for an overall system or set of prostheses, wherein such sets of prostheses are more anatomically optimized for the female anatomy as compared with the sets of known prostheses.

Furthermore, from the data in Table 5, it may be seen that there is a significant difference in slope for the sets of prostheses of Embodiments 3, 4, and 5 as compared with the slopes of the known sets of prostheses when looking at the B-B and MB dimensions. The magnitudes of the B-B values and MB values for a given A/P dimension are more pronounced, i.e., the variance in width at dimension B-B or MB over various A/P sizes between the sets of prostheses of Embodiments 3, 4, and 5 and the known sets of prostheses is more dramatically pronounced.

Specifically, sets of prostheses of Embodiments 3, 4, and 5 have a narrowing B-B M/L dimension with increasing A/P size, as indicated by slopes less than approximately 0.77, for example, as opposed to a substantially parallel or one-to-one relationship between the B-B M/L dimension and the A/P dimension with increasing A/P size as in the sets of known prostheses, as indicated by slopes of 0.78 and above. In exemplary embodiments, the slope of the B-B M/L dimension with increasing A/P size for prostheses 50 may be as small as approximately 0.30, 0.35, 0.40, or 0.45 or as large as 0.77, 0.76, 0.75, 0.74, 0.72, 0.70, 0.65, 0.60, or 0.50. In an exemplary embodiment, the slope is of the B-B M/L dimension with increasing A/P size for prostheses 50 is approximately 0.46. Thus, the B-B M/L dimension for prostheses 50 increases at a lesser rate than the corresponding overall A/P dimension. In contrast, in the sets of known prostheses, the B-B M/L dimension and the A/P dimension increase at substantially the same rate with increasing A/P size.

Furthermore, sets of prostheses of Embodiments 3, 4, and 5 have a narrowing MB M/L dimension with increasing A/P size, as indicated by slopes less than 0.76, for example, as opposed to a substantially parallel or one-to-one relationship between the MB M/L dimension and the A/P dimension with increasing A/P size as in the sets of known prostheses, as indicated by slopes of 0.77 and above. In exemplary embodiments, the slope of the MB M/L dimension with increasing A/P size for prostheses 50 may be as small as approximately 0.40, 0.45, 0.50, 0.55, or 0.57 or as large as approximately 0.76, 0.75, 0.74 0.73, 0.72, 0.71, 0.70, 0.65, or 0.60. In an exemplary embodiment, the slope of the MB M/L dimension with increasing A/P size for prostheses 50 is approximately 0.60. Thus, the MB M/L dimension for prostheses 50 increases at a lesser rate than the corresponding overall A/P dimension. In contrast, in the sets of known prostheses, the MB M/L dimension and the A/P dimension increase at substantially the same rate with increasing A/P size.

In this manner, the prostheses designed in accordance with the present invention offer a surgeon a unique combination of implant M/L widths as an overall system of prostheses, wherein such sets of prostheses are more anatomically optimized for the female anatomy as compared with the sets of known prostheses.

Referring again to FIG. 6, the range of values for Embodiment 5 generally falls within the lines of a conceptual boundary, such as a parallelogram, as shown in solid dashed lines. Clearly, no other known prostheses have MB M/L dimensions that fall within this range of values for the MB M/L dimensions and corresponding Overall A/P dimensions. The parallelogram is essentially defined by four points defined by coordinates given by (Overall A/P dimension, MB Dimension): A first point or upper left corner ("First Point")—(52.0, 55.0); A second point or lower left corner ("Second Point")—(52.0, 47.0); A third point or upper right corner ("Third Point")—(77.0, 78.5); and a fourth point or lower right corner ("Fourth Point")—(77.0, 70.0). Thus, the upper boundary of the parallelogram defined by First Point and Third Point may be given by the equation MB M/L=0.94*Overall A/P+6.12 and the lower boundary defined by Second Point and Fourth Point may be given by the equation MB M/L=0.92*Overall A/P−0.84.

As set forth in Table 6 below, the Overall A/P dimensions and the ratios of the dimensions "Posterior", "MB", and "B-B" vs. "Overall A/P" are given for Embodiments 3, 4, and 5 as well as for conventional prostheses Conventional 3, 4, and 5.

TABLE 6

| SIZE | Overall A/P | Ratio (Posterior M/L/ Overall A/P) | Ratio (MB M/L/ Overall A/P) | Ratio (B-B M/L/ Overall A/P) | Overall A/P | Ratio (Posterior M/L/ Overall A/P) | Ratio (MB M/L/ Overall A/P) | Ratio (B-B M/L/ Overall A/P) |
|---|---|---|---|---|---|---|---|---|
| | Embodiment 4 | | | | Conventional 4 | | | |
| C | 53.3 | 1.09 | 1.05 | 0.94 | 54.4 | 1.10 | 1.08 | 0.98 |
| D | 57.5 | 1.07 | 1.02 | 0.91 | 58.6 | 1.09 | 1.06 | 0.95 |
| E | 61.2 | 1.06 | 0.99 | 0.88 | 62.5 | 1.09 | 1.05 | 0.95 |
| F | 65.3 | 1.04 | 0.97 | 0.86 | 66.5 | 1.08 | 1.06 | 0.95 |
| G | 70.4 | 1.02 | 0.94 | 0.82 | 71.5 | 1.07 | 1.04 | 0.94 |
| | Embodiment 3 | | | | Conventional 3 | | | |
| C | 52.3 | 1.11 | 1.07 | 0.96 | 53.5 | 1.12 | 1.09 | 1.00 |
| D | 56.4 | 1.09 | 1.04 | 0.92 | 57.6 | 1.11 | 1.08 | 0.97 |
| E | 60.2 | 1.08 | 1.01 | 0.90 | 61.5 | 1.11 | 1.07 | 0.96 |
| F | 64.2 | 1.06 | 0.99 | 0.87 | 65.5 | 1.10 | 1.07 | 0.97 |
| G | 69.4 | 1.03 | 0.95 | 0.84 | 70.5 | 1.09 | 1.05 | 0.95 |
| | Embodiment 5 | | | | Conventional 5 | | | |
| C | 52.8 | 1.10 | 1.06 | 0.95 | 54.0 | 1.11 | 1.09 | 0.99 |
| D | 56.9 | 1.08 | 1.03 | 0.91 | 58.1 | 1.10 | 1.07 | 0.96 |
| E | 60.7 | 1.07 | 1.00 | 0.89 | 62.0 | 1.10 | 1.06 | 0.96 |
| F | 64.8 | 1.05 | 0.98 | 0.86 | 66.0 | 1.09 | 1.06 | 0.96 |
| G | 69.9 | 1.02 | 0.94 | 0.83 | 71.0 | 1.08 | 1.04 | 0.95 |

FIG. 9 is a graph of the ratio of (MB M/L/Overall A/P) vs. Overall A/P for the prostheses described above with respect to FIG. 6. FIG. 10 is a graph of the ratio of (B-B M/L/Overall A/P) vs. Overall A/P for the prostheses described above with respect to FIG. 7. FIG. 11 is a graph of the ratio of (Posterior M/L/Overall A/P) vs. Overall A/P for the prostheses described above with respect to FIG. 8.

Table 7 below sets forth the results of a first order equation fit to each of the data sets shown in FIGS. 9, 10, and 11 as well as for the data sets of Embodiments 3 and 4 and Conventional 3 and 4 in Table 6.

ments 3, 4, and 5 as compared to the slopes of the sets of the known prostheses. In particular, it may be seen from the data in Table 7 that the sets of prostheses of Embodiments 3, 4, and 5 have a narrowing posterior M/L dimension with increasing A/P size, as indicated by the slope of the ratio (posterior M/L/overall A/P) vs. overall A/P being less than −0.0032 for the sets of prostheses of Embodiments 3, 4, and 5 while the corresponding slope for the known sets of prostheses is greater than or equal to −0.0032, except for the Competitive 7 prosthesis, indicating that the sets of prostheses of Embodiments 3, 4, and 5 have an increasingly more pronounced narrowing of the posterior M/L dimension with increasing A/P size. In this manner, the sets of prostheses designed in accordance with the present invention

TABLE 7

| | Ratio (Posterior M/L vs. Overall A/p) vs. Overall A/P Best Fit Regression Line | | Ratio (Mid-box M/L vs. Overall A/P) vs. Overall A/P Best Fit Regression Line | | Ratio (B-B M/L vs. Overall A/P) vs. Overall A/P Best Fit Regression Line | |
|---|---|---|---|---|---|---|
| Implant | Slope | y-Intercept | Slope | y-Intercept | Slope | y-Intercept |
| Conventional 3 | −0.0020 | 1.23 | −0.0023 | 1.21 | −0.0023 | 1.11 |
| Conventional 4 | −0.0017 | 1.20 | −0.0020 | 1.18 | −0.0020 | 1.08 |
| Conventional 5 | −0.0018 | 1.21 | −0.0021 | 1.20 | −0.0022 | 1.10 |
| Embodiment 3 | −0.0044 | 1.34 | −0.0068 | 1.42 | −0.0071 | 1.33 |
| Embodiment 4 | −0.0041 | 1.31 | −0.0064 | 1.39 | −0.0068 | 1.30 |
| Embodiment 5 | −0.0042 | 1.32 | −0.0066 | 1.41 | −0.0069 | 1.31 |
| Competitive 1 | −0.0003 | 1.10 | −0.0008 | 1.11 | −0.0004 | 0.99 |
| Competitive 2 | −0.0017 | 1.20 | 0.0003 | 1.06 | −0.0032 | 1.21 |
| Competitive 3 | −0.0013 | 1.15 | −0.0003 | 1.09 | −0.0024 | 1.14 |
| Competitive 4 | −0.0016 | 1.18 | −0.0009 | 1.13 | −0.0001 | 1.07 |
| Competitive 5 | −0.0032 | 1.32 | −0.0032 | 1.31 | −0.0025 | 1.15 |
| Competitive 6 | −0.0001 | 1.08 | 0.0001 | 1.06 | 0.0010 | 0.94 |
| Competitive 7 | −0.0053 | 1.51 | −0.0054 | 1.43 | −0.0024 | 1.08 |
| Competitive 8 | 0.0001 | 0.89 | 0.0004 | 0.86 | 0.0006 | 0.83 |

From the data in Table 7 it may be seen that there is a difference in the slopes of the sets of prostheses of Embodioffer a surgeon a unique combination of implant posterior M/L widths with varying A/P size for an overall system or set of prostheses, wherein such sets of prostheses are more anatomically optimized for the female anatomy as compared with the sets of known prostheses.

Furthermore, it may be seen that there is a significant difference in slope for the sets of prostheses of Embodiments 3, 4, and 5 as compared with the slopes of the known sets of prostheses when looking at the MB and B-B M/L dimensions. The magnitudes of the anterior M/L "B-B" values for a given A/P dimension are more pronounced, i.e., the variance in width at dimension B-B, namely, an anterior width, over various A/P sizes between the sets of prostheses of Embodiments 3, 4, and 5 and the known sets of prostheses is more dramatically pronounced. Specifically, the slope of the ratio (B-B M/L/overall A/P) vs. overall A/P is less than −0.0032 for the sets of prostheses of Embodiments 3, 4, and 5, while the corresponding slope for the known sets of prostheses is greater than or equal to −0.0032, indicating that the sets of prostheses of Embodiments 3, 4, and 5 have increasingly more pronounced narrowing of the B-B M/L dimension with increasing A/P size.

Furthermore, the slope of the ratio (MB M/L/Overall A/P) vs. Overall A/P is less than −0.0054 for the sets of prostheses of Embodiments 3, 4, and 5, while the corresponding slope for the known sets of prostheses is greater than or equal to −0.0054, indicating that the sets of prostheses of Embodiments 3, 4, and 5 have increasingly more pronounced narrowing of the B-B M/L dimension with increasing A/P size. Prostheses 50 may have slope values for the ratios of MB M/L/Overall A/P vs. Overall A/P with increasing A/P size which may be as small as −0.0075, −0.0072, −0.0069, −0.0066, or −0.0063 or as large as −0.0055, −0.0057, −0.0059, or −0.0061. In this manner, the prostheses designed in accordance with the present invention offer a surgeon a unique combination of implant M/L widths as an overall system of prostheses, wherein such sets of prostheses are more anatomically optimized for the female anatomy as compared with the sets of known prostheses.

Referring again to FIG. 9, the range of values for Embodiment 5 generally falls within the lines of a conceptual boundary, such as a four-sided polygon, as shown in solid dashed lines. Clearly, no other known prostheses have MB M/L/Overall A/P ratios that fall within this range of values for the MB M/L/Overall A/P ratios and corresponding Overall A/P dimensions. The polygon is essentially defined by four points defined by coordinates given by (Overall A/P dimension, MB M/L/Overall A/P ratio): A first point or upper left corner ("First Point")—(52.0, 1.06); A second point or lower left corner ("Second Point")—(52.0, 0.90); A third point or upper right corner ("Third Point")—(77.0, 1.02); and a fourth point or lower right corner ("Fourth Point")—(77.0, 0.91). Thus, the upper boundary of the parallelogram defined by First Point and Third Point may be given by the equation MB M/L/Overall A/P Ratio=−0.0015*Overall A/P+1.14 and the lower boundary defined by Second Point and Fourth Point may be given by the equation MB M/L/Overall A/P Ratio=0.0002*Overall A/P+0.89.

As another exemplary comparison, the dimensions "A-A" and "Overall A/P" for conventional prostheses ("Conventional 3", "Conventional 4", and "Conventional 5" including five increasing sizes C through G) are compared with corresponding dimensions of a set of prostheses designed in accordance with the present invention ("Embodiment 3", "Embodiment 4", and "Embodiment 5" including five increasing sizes C through G). In one embodiment, the values for Conventional 5 and Embodiment 5 may be average values of Conventionals 3 and 4 and Embodiments 3 and 4, respectively. These values are presented in Table 8 below.

TABLE 8

| SIZE | Overall A/P | A-A | Overall A/P | A-A |
|---|---|---|---|---|
| | Embodiment 4 | | Conventional 4 | |
| C | 53.3 | 41.0 | 54.4 | 45.0 |
| D | 57.5 | 42.6 | 58.6 | 46.3 |
| E | 61.2 | 43.6 | 62.5 | 48.9 |
| F | 65.3 | 44.9 | 66.5 | 51.7 |
| G | 70.4 | 46.1 | 71.5 | 56.0 |
| | Embodiment 3 | | Conventional 3 | |
| C | 52.3 | 41.0 | 53.5 | 45.0 |
| D | 56.4 | 42.6 | 57.6 | 46.4 |
| E | 60.2 | 43.6 | 61.5 | 48.5 |
| F | 64.2 | 44.9 | 65.5 | 51.6 |
| G | 69.4 | 46.1 | 70.5 | 55.7 |
| | Embodiment 5 | | Conventional 5 | |
| C | 52.8 | 41.0 | 54.0 | 45.0 |
| D | 56.9 | 42.6 | 58.1 | 46.3 |
| E | 60.7 | 43.6 | 62.0 | 48.7 |
| F | 64.8 | 44.9 | 66.0 | 51.7 |
| G | 69.9 | 46.1 | 71.0 | 55.8 |

FIG. 18 is a graph of the dimension A-A M/L vs. overall A/P for the following sets of prostheses, each in increasing sizes C through G: Conventional 5, Embodiment 5, as well as eight other sets of known competitive prostheses, designated Competitive 1, Competitive 2, Competitive 3, Competitive 4, Competitive 5, Competitive 6, Competitive 7, and Competitive 8.

Table 9 below sets forth the results of a first order equation fit to the data sets shown in FIG. 18 as well as for the data sets of Embodiments 3 and 4 and Conventional 3 and 4 in Table 8.

TABLE 9

| | A-A M/L vs. Overall A/P Best Fit Regression Line | |
|---|---|---|
| Implant | Slope | y-Intercept |
| Conventional 3 | 0.64 | 9.66 |
| Conventional 4 | 0.65 | 8.59 |
| Conventional 5 | 0.65 | 9.13 |
| Embodiment 3 | 0.30 | 25.78 |
| Embodiment 4 | 0.30 | 25.47 |
| Embodiment 5 | 0.30 | 25.63 |
| Competitive 1 | 0.54 | 13.20 |
| Competitive 2 | 0.46 | 19.33 |
| Competitive 3 | 0.68 | 9.93 |
| Competitive 4 | 0.76 | 6.05 |
| Competitive 5 | 0.28 | 30.74 |
| Competitive 6 | 0.86 | 2.98 |
| Competitive 7 | 0.68 | 6.54 |
| Competitive 8 | 0.57 | 13.19 |

From the data in Table 9, it may be seen that there is a difference in the slopes of the sets of prostheses of Embodiments 3, 4, and 5 as compared to the slopes of the sets of the known prostheses. In particular, it may be seen from the data in Table 9 that the sets of prostheses of Embodiments 3, 4, and 5 have a narrowing A-A M/L dimension with increasing A/P size, as indicated by slopes less than approximately 0.46, except for Competitive 5, for example, as opposed to a substantially parallel or one-to-one relationship between the posterior M/L dimension and the A/P dimension with increasing A/P size as in the sets of known prostheses, as indicated by slopes greater than or equal 0.46. In an exemplary embodiment, the slope of A-A M/L dimension with increasing A/P size for prostheses 50 is approximately 0.30.

As set forth in Table 10 below, the Overall A/P dimensions and the ratios of the dimension "A-A" vs. "Overall A/P" are given for Embodiments 3, 4, and 5 as well as for conventional prostheses Conventional 3, 4, and 5.

TABLE 10

| SIZE | Overall A/P | Ratio (A-A M/L/ Overall A/P) | Overall A/P | Ratio (A-A M/L/ Overall A/P) |
|---|---|---|---|---|
| | Embodiment 4 | | Conventional 4 | |
| C | 53.3 | 0.77 | 54.4 | 0.83 |
| D | 57.5 | 0.74 | 58.6 | 0.79 |
| E | 61.2 | 0.71 | 62.5 | 0.78 |
| F | 65.3 | 0.69 | 66.5 | 0.78 |
| G | 70.4 | 0.66 | 71.5 | 0.78 |
| | Embodiment 3 | | Conventional 3 | |
| C | 52.3 | 0.78 | 53.5 | 0.84 |
| D | 56.4 | 0.76 | 57.6 | 0.81 |
| E | 60.2 | 0.72 | 61.5 | 0.79 |
| F | 64.2 | 0.70 | 65.5 | 0.79 |
| G | 69.4 | 0.66 | 70.5 | 0.79 |
| | Embodiment 5 | | Conventional 5 | |
| C | 52.8 | 0.78 | 54.0 | 0.83 |
| D | 56.9 | 0.75 | 58.1 | 0.80 |
| E | 60.7 | 0.72 | 62.0 | 0.78 |
| F | 64.8 | 0.69 | 66.0 | 0.78 |
| G | 69.9 | 0.66 | 71.0 | 0.79 |

FIG. 19 is a graph of the ratio of (A-A M/L/Overall A/P) vs. Overall A/P for the prostheses described above with respect to FIG. 18.

Table 11 below sets forth the results of a first order equation fit to the data sets shown in FIG. 19 as well as for the data sets of Embodiments 3 and 4 and Conventional 3 and 4 in Table 10.

TABLE 11

| | Ratio (A-A M/L vs. Overall A/P) vs. Overall A/P Best Fit Regression Line | |
|---|---|---|
| Implant | Slope | y-Intercept |
| Conventional 3 | −0.0027 | 0.97 |
| Conventional 4 | −0.0023 | 0.94 |
| Conventional 5 | −0.0025 | 0.95 |
| Embodiment 3 | −0.0071 | 1.15 |
| Embodiment 4 | −0.0067 | 1.13 |
| Embodiment 5 | −0.0069 | 1.14 |
| Competitive 1 | −0.0031 | 0.94 |
| Competitive 2 | −0.0049 | 1.08 |
| Competitive 3 | −0.0024 | 0.99 |
| Competitive 4 | −0.0016 | 0.96 |
| Competitive 5 | −0.0073 | 1.24 |
| Competitive 6 | 0.0007 | 0.77 |
| Competitive 7 | −0.0019 | 0.90 |
| Competitive 8 | −0.0033 | 0.99 |

From the data in Table 11 it may be seen that there is a difference in the slopes of the sets of prostheses of Embodiments 3, 4, and 5 as compared to the slopes of the sets of the known prostheses. In particular, it may be seen from the data in Table 7 that the sets of prostheses of Embodiments 3, 4, and 5 have a narrowing A-A M/L dimension with increasing A/P size, as indicated by the slope of the ratio (A-A M/L/overall A/P) vs. overall A/P being less than −0.0049, for the sets of prostheses of Embodiments 3, 4, and 5 while the corresponding slope for the known sets of prostheses is greater than or equal to −0.0049, except for the Competitive 5 prosthesis, indicating that the sets of prostheses of Embodiments 3, 4, and 5 have an increasingly more pronounced narrowing of the A-A M/L dimension with increasing A/P size. In this manner, the sets of prostheses designed in accordance with the present invention offer a surgeon a unique combination of implant A-A M/L widths with varying A/P size for an overall system or set of prostheses, wherein such sets of prostheses are more anatomically optimized for the female anatomy as compared with the sets of known prostheses.

Referring again to FIG. 18, the range of values for Embodiment 5 generally falls below the line of a conceptual boundary. The boundary may be defined by two points defined by coordinates given by (Overall A/P dimension, A-A M/L dimension): a First Point (52.0, 40.3) and a Second Point (77.0, 51.8). Thus, the boundary defines a line given by the following equation: A-A M/L=0.46*Overall A/P+16.38.

Referring again to FIG. 19, the range of values for Embodiment 5 generally falls below the line of a conceptual boundary. The boundary may be defined by two points defined by coordinates given by (Overall A/P dimension, A-A M/L/Overall A/P ratio): a First Point (52.0, 0.78) and a Second Point (77.0, 0.67). Thus, the boundary defines a line given by the following equation: A-A M/L/Overall A/P=−0.0041*Overall A/P+0.99.

Figure 12:
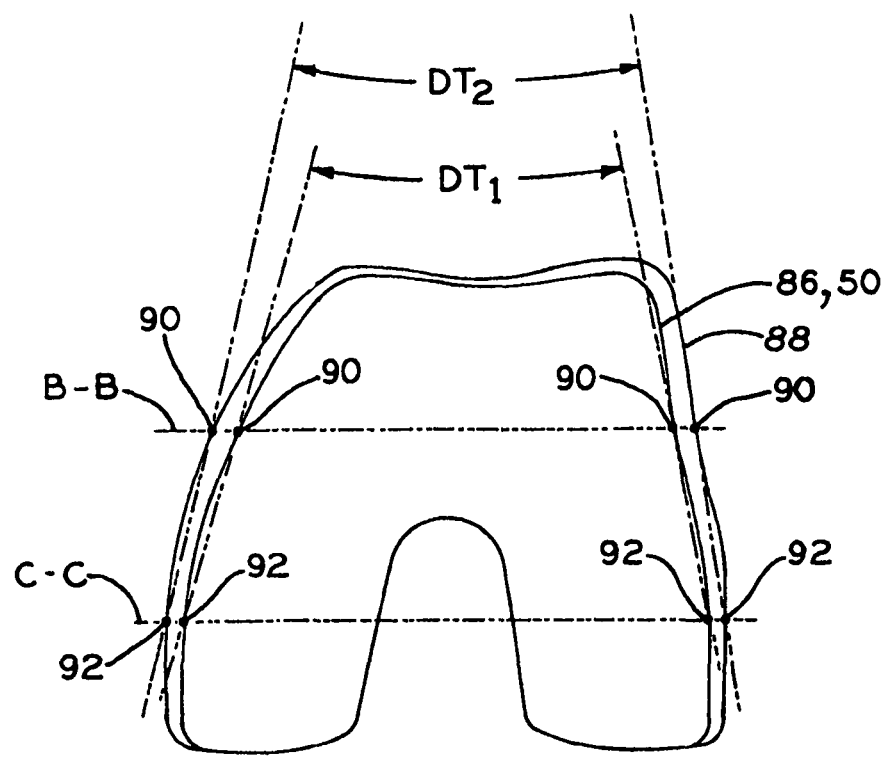
FIG. 12 is a distal view of an exemplary prosthesis designed in accordance with the present invention, shown superimposed on a known prosthesis and illustrating the profiles and the distal taper angles of same.

Another way of characterizing the design of the present prostheses is by distal taper angle, "DT". As used herein and referring to FIG. 12, in which the profile 86 of prosthesis 50 is superimposed upon profile 88 of a known prosthesis, the distal taper angle "DT" is the angle between two lines on opposite sides of the prosthesis each connecting a point 90 on the edge of the anterior distal chamfer, i.e., along dimension "B-B" and a point 92 on the edge of the posterior distal chamfer, i.e., along dimension "C-C". In FIG. 12, distal taper angles $DT_1$ and $DT_2$ for prosthesis 50 and for a known prosthesis are illustrated, respectively. It may be seen from FIG. 12 that the distal taper angle $DT_1$ for prosthesis 50 is greater than the distal taper angle $DT_2$ for the known prosthesis.

Figure 13:
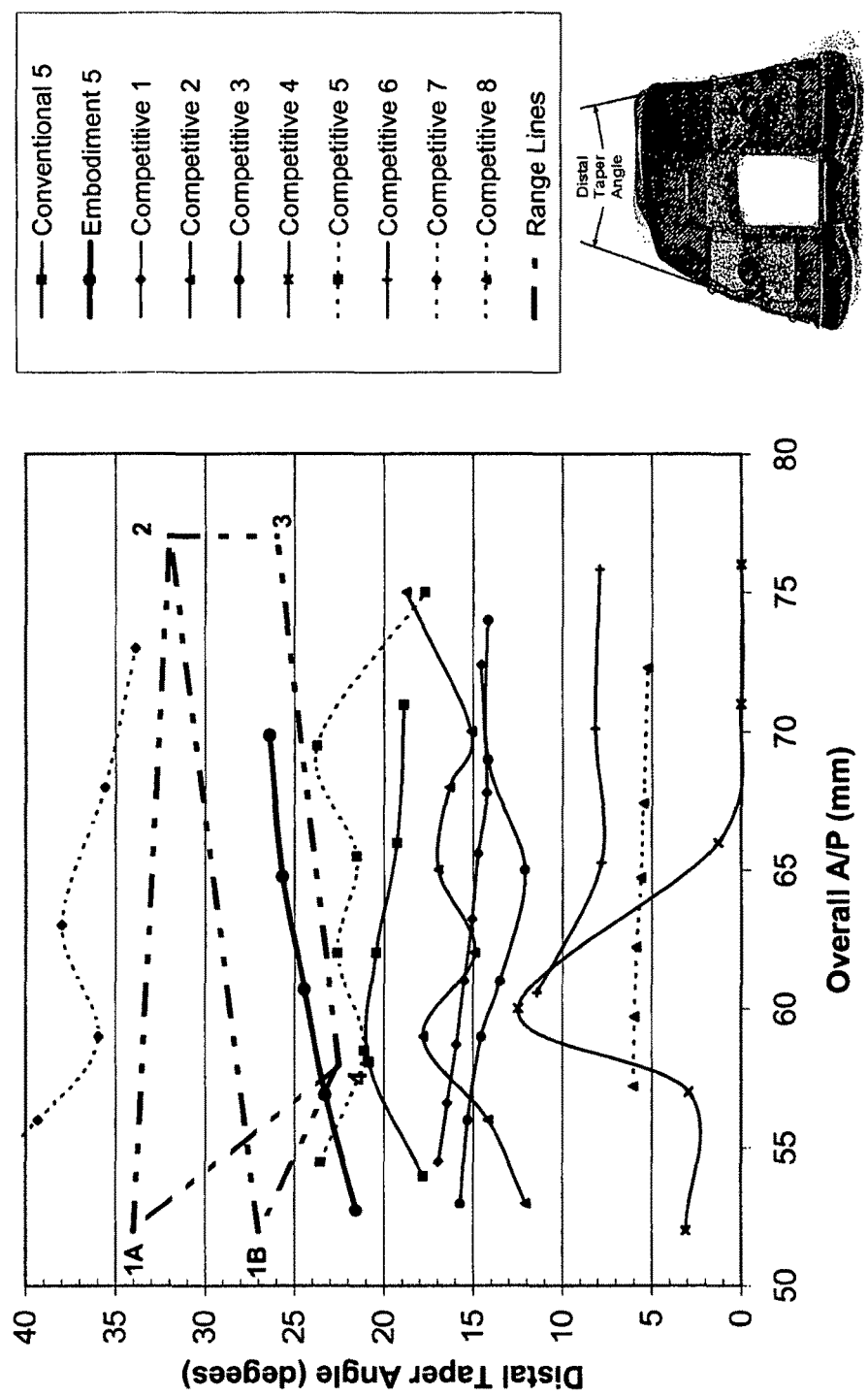
FIG. 13 is a graph of distal taper angle vs. overall A/P for prostheses designed in accordance with the present invention as compared with several known prostheses.

FIG. 13 is a chart of distal taper angle vs. overall A/P for several of the prostheses described above. As before, a first order curve fit was applied to the data in FIG. 13 and the results are set forth below in Table 12.

TABLE 12

| | Distal Taper Angle vs. Overall A/P Best fit regression line | |
|---|---|---|
| | Equation | Slope |
| Conventional 3 | y = 0.01x + 18.72 | 0.01 |
| Conventional 4 | y = 0.01x + 18.79 | 0.01 |
| Conventional 5 | y = 0.01x + 17.75 | 0.01 |
| Embodiment 3 | y = 0.28x + 7.10 | 0.28 |
| Embodiment 4 | y = 0.28x + 6.80 | 0.28 |
| Embodiment 5 | y = 0.28x + 6.95 | 0.28 |
| Competitive 1 | y = −0.15x + 24.81 | −0.15 |
| Competitive 2 | y = 0.20x + 3.04 | 0.20 |
| Competitive 3 | y = −0.08x + 19.43 | −0.08 |
| Competitive 4 | y = −0.24x + 18.77 | −0.24 |
| Competitive 5 | y = −0.18x + 33.07 | −0.18 |
| Competitive 6 | y = −0.19x + 21.99 | −0.19 |
| Competitive 7 | y = −0.48x + 67.89 | −0.48 |
| Competitive 8 | y = −0.06x + 9.37 | −0.06 |

As may be seen from the data in Table 12, the ratio between distal taper angle and overall A/P of the prostheses of Embodiments 3-5 differs from the known prostheses. In particular, the foregoing data indicates that prostheses of Embodiments 3-5 have a more pronounced and consistent increase in distal taper angle with increasing A/P size, as evidenced by a slope of greater than 0.20. Additionally, as may be seen from FIG. 13, the set of prostheses of Embodiment 5 has greater distal taper angles throughout the range of sizes of the prostheses than the known sets of prostheses with positive slopes as set forth in Table 12. Further, the distal taper angle curve for the set of prostheses of Embodiment 5 has a consistent upward slope as opposed to the randomized "see-saw" curves or flattened curves of the known sets of prostheses, indicating a more precise, parallel or substantial one-to-one relationship between distal taper angle and overall A/P with increasing A/P size for the set of prostheses of Embodiment 5. In exemplary embodiments, the slope of the distal taper angle with increasing A/P size for prostheses 50 may be as small as approximately 0.21, 0.22, 0.23, 0.24, 0.25, 0.26, 0.27, or 0.30 or as large as approximately 0.42, 0.39, 0.36, or 0.33. In an exemplary embodiment, the slope of the distal taper angle with increasing A/P size for prostheses 50 is approximately 0.28.

As shown in FIG. 13, the range of values for Embodiment 5 generally fall within the lines of a conceptual boundary, such as a four-sided polygon, as shown in solid dashed lines. Clearly, no other known prostheses have distal taper angle values that fall within this range of values for the distal taper angle and corresponding Overall A/P dimensions. The four-sided polygon is essentially defined by four points defined by coordinates given by (Overall A/P dimension, Distal Taper Angle): An upper left corner ("1B")—(52.0, 27.0°); A lower left corner ("4")—(58.0, 22.5°); An upper right corner ("2")—(77.0, 32.0°); and a lower right corner ("3")—(77.0, 26.0°). Alternatively, the upper left corner may be at coordinates (52.0, 34.0°) ("1A"). Alternatively, points 1A, 1B, 2, 3, and 4 define a five-sided polygon which defines the conceptual boundary. The distal taper angles for Embodiment 5 may be approximately equal to or greater than 21°. The values of distal taper angles for prostheses 50 may be as small as approximately 21°, 22°, 23°, 25°, or 27, as large as approximately 35°, 33°, 31°, or 29°.

Referring again to FIG. 8, the sets of prostheses may be grouped into a standard aspect ratio category and a non-standard aspect ratio category. As used herein, the term "standard aspect ratio" describes a set of prostheses which, for overall A/P values ranging from approximately 52.0 mm to 77.0 mm, have corresponding posterior M/L dimensions which generally fall between an Upper Boundary and a Lower Boundary. The Upper Boundary and Lower Boundary may be defined by lines having points defined by coordinates given by (Overall A/P dimension, Posterior M/L dimension). The Upper Boundary may be defined by a line connecting a first or lower left point ("First Upper Point")—(52.0, 59.0) and a second or upper right point ("Second Upper Point")—(77.0, 83.5). The Lower Boundary may be defined by three exemplary boundaries. In one exemplary embodiment, Lower Boundary 1 may be defined by a line connecting a first or lower left point ("First Lower Point 1")—(52.0, 51.0) and a second or upper right point ("Second Lower Point 1")—(77.0, 73.0). In another exemplary embodiment, Lower Boundary 2 may be defined by a line connecting a first or lower left point ("First Lower Point 2")—(52.0, 53.0) and a second or upper right point ("Second Lower Point 2")—(77.0, 75.0). In yet another exemplary embodiment, Lower Boundary 3 may be defined by a line connecting a first or lower left point ("First Lower Point 3")—(52.0, 55.0) and a second or upper right point ("Second Lower Point 3")—(77.0, 77.0). For prostheses having overall A/P values ranging from approximately 52.0 mm to 77.0 mm, the following equations may define the Upper and Lower Boundaries: the Upper Boundary line may be defined by the following equation: Posterior M/L=0.98*Overall A/P+8.04; the Lower Boundary 1 line may be defined by the following equation: Posterior M/L=0.88*Overall A/P+5.24; the Lower Boundary 2 line may be defined by the following equation: Posterior M/L=0.88*Overall A/P+7.24; and the Lower Boundary 3 line may be defined by the following equation: Posterior M/L=0.88*Overall A/P+9.24.

Referring again to FIG. 11, the Upper Boundary and Lower Boundary described above which are used to define the standard aspect ratio category for sets of prostheses may also be used with the posterior M/L/Overall A/P ratio for overall A/P values ranging from approximately 52.0 mm to 77.0 mm. The Upper Boundary and Lower Boundary may be defined by lines having points defined by coordinates given by (Overall A/P dimension, Posterior M/L/Overall A/P Ratio). The Upper Boundary may be defined by a line connecting a first or lower left point ("First Upper Point")—(52.0, 1.13) and a second or upper right point ("Second Upper Point")—(77.0, 1.08). The Lower Boundary may be defined by three exemplary boundaries. Lower Boundary 1 may be defined by a line connecting a first or lower left point ("First Lower Point 1")—(52.0, 0.98) and a second or upper right point ("Second Lower Point 1")—(77.0, 0.95). Lower Boundary 2 may be defined by a line connecting a first or lower left point ("First Lower Point 2")—(52.0, 1.02) and a second or upper right point ("Second Lower Point 2")—(77.0, 0.97). Lower Boundary 3 may be defined by a line connecting a first or lower left point ("First Lower Point 3")—(52.0, 1.06) and a second or upper right point ("Second Lower Point 3")—(77.0, 1.00). For prostheses having overall A/P values ranging from approximately 52.0 mm to 77.0 mm, the following equations may define the Upper and Lower Boundaries: the Upper Boundary line may be defined by the following equation: Posterior M/L/Overall A/P=−0.0020*Overall A/P+1.24; the Lower Boundary 1 line may be defined by the following equation: Posterior M/L/Overall A/P=−0.0013*Overall A/P+1.05; the Lower Boundary 2 line may be defined by the following equation: Posterior M/L/Overall A/P=−0.0018*Overall A/P+1.11; and the Lower Boundary 3 line may be defined by the following equation: Posterior M/L/Overall A/P=−0.0023*Overall A/P+1.18.

Referring to FIGS. 8 and 11 and applying the foregoing definition of standard aspect ratio, it may be seen that the prostheses described by Competitive 5, Competitive 7, and Competitive 8 fall within the non-standard aspect ratio category.

Referring again to FIG. 13, Embodiment 5 has a distal taper angle greater than or equal to 21°. In contrast, all other standard aspect ratio prostheses have a distal taper angle less than 21°.

Referring again to FIG. 6, Embodiment 5 has MB M/L dimensions below the boundary defined by a line connecting the First Point (52.0, 55.0) and the Third Point (77.0, 78.5). Thus, for the range of Overall A/P values between 52.0 and 77.0, Embodiment 5 has MB M/L dimensions which fall below the line given by the following equation: MB M/L=0.94*Overall A/P+6.12. In contrast, all other standard aspect ratio prostheses have MB M/L dimensions which fall above the line given by the foregoing equation.

Referring again to FIG. 9, Embodiment 5 has MB M/L/Overall A/P ratios below the boundary defined by a line connecting the First Point (52.0, 1.06) and the Third Point (77.0, 1.02). Thus, for the range of Overall A/P values between 52.0 and 77.0, Embodiment 5 has MB M/L/Overall A/P ratios which fall below the line given by the following equation: MB M/L/Overall A/P=−0.0015*Overall A/P+ 1.14. In contrast, all other standard aspect ratio prostheses have MB M/L/Overall A/P ratios which fall above the line given by the foregoing equation.

Referring again to FIG. 7, Embodiment 5 has B-B M/L dimensions below the boundary defined by a line connecting the First Point (52.0, 50.0) and the Second Point (77.0, 70.5). Thus, for the range of Overall A/P values between 52.0 and 77.0, Embodiment 5 has B-B M/L dimensions which fall below the line given by the following equation: B-B M/L=0.82*Overall A/P+7.36. In contrast, all other standard aspect ratio prostheses have B-B M/L dimensions which fall above the line given by the foregoing equation.

Referring again to FIG. 10, Embodiment 5 has B-B M/L/Overall A/P ratios below the boundary defined by a line connecting the First Point (52.0, 0.96) and the Second Point (77.0, 0.92). Thus, for the range of Overall A/P values between 52.0 and 77.0, Embodiment 5 has B-B M/L/Overall A/P ratios which fall below the line given by the following equation: B-B M/L/Overall A/P=−0.0018*Overall A/P+ 1.06. In contrast, all other standard aspect ratio prostheses have B-B M/L/Overall A/P ratios which fall above the line given by the foregoing equation.

Referring again to FIG. 18, Embodiment 5 has A-A M/L dimensions below the boundary defined by a line connecting the Third Point (52.0, 40.1) and the Fourth Point (77.0, 53.5). Thus, for the range of Overall A/P values between 52.0 and 77.0, Embodiment 5 has A-A M/L dimensions which fall below the line given by the following equation: A-A M/L=0.54*Overall A/P+12.23. In contrast, all other standard aspect ratio prostheses have A-A M/L dimensions which fall above the line given by the foregoing equation.

Referring again to FIG. 19, Embodiment 5 has A-A M/L/Overall A/P ratios below the boundary defined by a line connecting the Third Point (52.0, 0.77) and the Fourth Point (77.0, 0.69). Thus, for the range of Overall A/P values between 52.0 and 77.0, Embodiment 5 has A-A M/L/Overall A/P ratios which fall below the line given by the following equation: A-A M/L/Overall A/P=−0.0031*Overall A/P+ 0.93. In contrast, all other standard aspect ratio prostheses have A-A M/L/Overall A/P ratios which fall above the line given by the foregoing equation.

Referring again to Table 5, Embodiments 3-5 have slopes of Posterior M/L dimension with increasing A/P size which are less than 0.98. Prostheses 50 may have slope values for the Posterior M/L dimension with increasing A/P size which may be as small as approximately 0.50, 0.55, 0.60, or 0.65 or as large as approximately 0.96, 0.95, 0.94, 0.91, 0.88, 0.85, 0.84, 0.83, 0.81, 0.80, 0.75, or 0.70. In contrast, all other standard aspect ratio prostheses have slopes of Posterior M/L dimension with increasing A/P size which are greater than or equal to 0.98.

Referring still to Table 5, Embodiments 3-5 have slopes of MB M/L dimension with increasing A/P size which are less than 0.91. Prostheses 50 may have slope values for the MB M/L dimension with increasing A/P size which may be as small as approximately 0.40, 0.45, 0.50, 0.55, or 0.57 or as large as approximately 0.90, 0.89, 0.87, 0.84, 0.81, 0.79, 0.76, 0.75, 0.74, 0.73, 0.72, 0.71, 0.70, 0.65, or 0.60. In contrast, all other standard aspect ratio prostheses have slopes of MB M/L dimension with increasing A/P size which are greater than or equal to 0.91.

Referring again to Table 5, Embodiments 3-5 have slopes of B-B M/L dimension with increasing A/P size which are less than 0.80. Prostheses 50 may have slope values for the B-B M/L dimension with increasing A/P size which may be as small as approximately 0.30, 0.35, 0.40, or 0.45 or as large as 0.79, 0.78, 0.77, 0.76, 0.75, 0.74, 0.72, 0.70, 0.65, 0.60, or 0.50. In contrast, all other standard aspect ratio prostheses have slopes of B-B M/L dimension with increasing A/P size which are greater than or equal to 0.80.

Referring to Table 9, Embodiments 3-5 have slopes of A-A M/L dimension with increasing A/P size which are less than 0.46. Prostheses 50 may have slope values for the A-A M/L dimension with increasing A/P size which may be as small as 0.15, 0.20, 0.25, or 0.30 or as large as 0.45, 0.44, 0.42, 0.40, 0.37, 0.34, or 0.31. In contrast, all other standard aspect ratio prostheses have slopes of A-A M/L dimension with increasing A/P size which are greater than or equal to 0.46.

Referring to Table 7, Embodiments 3-5 have slopes for the ratios of Posterior M/L/Overall A/P vs. Overall A/P with increasing A/P size which are less than −0.0020. Prostheses 50 may have slope values for the ratios of Posterior M/L/Overall A/P vs. Overall A/P with increasing A/P size which may be as small as −0.0060, −0.0055, −0.0050, −0.0045, −0.0040 or as large as −0.0021, −0.0022, −0.0025, −0.0030, or −0.0035. In contrast, all other standard aspect ratio prostheses have slopes for the ratios of Posterior M/L/Overall A/P vs. Overall A/P with increasing A/P size which are greater than or equal to −0.0020.

Referring again to Table 7, Embodiments 3-5 have slopes for the ratios of MB M/L/Overall A/P vs. Overall A/P with increasing A/P size which are less than −0.0023. Prostheses 50 may have slope values for the ratios of MB M/L/Overall A/P vs. Overall A/P with increasing A/P size which may be as small as −0.0075, −0.0072, −0.0069, −0.0066, or −0.0063 or as large as −0.0022, −0.0025, −0.0030, −0.0035, −0.0040, −0.0045, −0.0050, −0.0055, or −0.0060. In contrast, all other standard aspect ratio prostheses have slopes for the ratios of MB M/L/Overall A/P vs. Overall A/P with increasing A/P size which are greater than or equal to −0.0023.

Referring again to Table 7, Embodiments 3-5 have slopes for the ratios of B-B M/L/Overall A/P vs. Overall A/P with increasing A/P size which are less than −0.0032. Prostheses 50 may have slope values for the ratios of B-B M/L/Overall A/P vs. Overall A/P with increasing A/P size which may be as small as −0.0085, −0.0080, −0.0075, or −0.0070 or as large as −0.0031, −0.0032, −0.0034, −0.0037, −0.0040, −0.0045, −0.0050, −0.0055, −0.0060, or −0.0065. In an exemplary embodiment, the slope value for the ratio of B-B M/L/Overall A/P vs. Overall A/P with increasing A/P size is approximately −0.0069. In another exemplary embodiment, the slope value for the ratio of B-B M/L/Overall A/P vs. Overall A/P with increasing A/P size is approximately −0.0068. In yet another exemplary embodiment, the slope value for the ratio of B-B M/L/Overall A/P vs. Overall A/P with increasing A/P size is approximately −0.0071. In contrast, all other prostheses have slopes for the ratios of B-B M/L/Overall A/P vs. Overall A/P with increasing A/P size which are greater than or equal to −0.0032.

Referring again to Table 11, Embodiments 3-5 have slopes for the ratios of A-A M/L/Overall A/P vs. Overall A/P with increasing A/P size which are less than −0.0049. Prostheses 50 may have slope values for the ratios of A-A M/L/Overall A/P vs. Overall A/P with increasing A/P size which may be as small as −0.0080, −0.0075, −0.0070, or −0.0065 or as large as −0.0050, −0.0051, −0.0053, −0.0055, or −0.0060. In contrast, all other standard aspect ratio prostheses have slopes for the ratios of A-A M/L/Overall A/P vs. Overall A/P with increasing A/P size which are greater than or equal to −0.0049.

In accordance with another aspect of the present invention, the prosthesis 50 includes a recessed or reduced profile patellar sulcus as well as a thinned or reduced profile anterior flange condyles in comparison with known prostheses to alleviate the potential for the thicknesses of the patellar sulcus and the anterior flange condyles to be greater than the thickness of the femoral bone which is resected during the TKR/TKA procedure.

Figure 14:
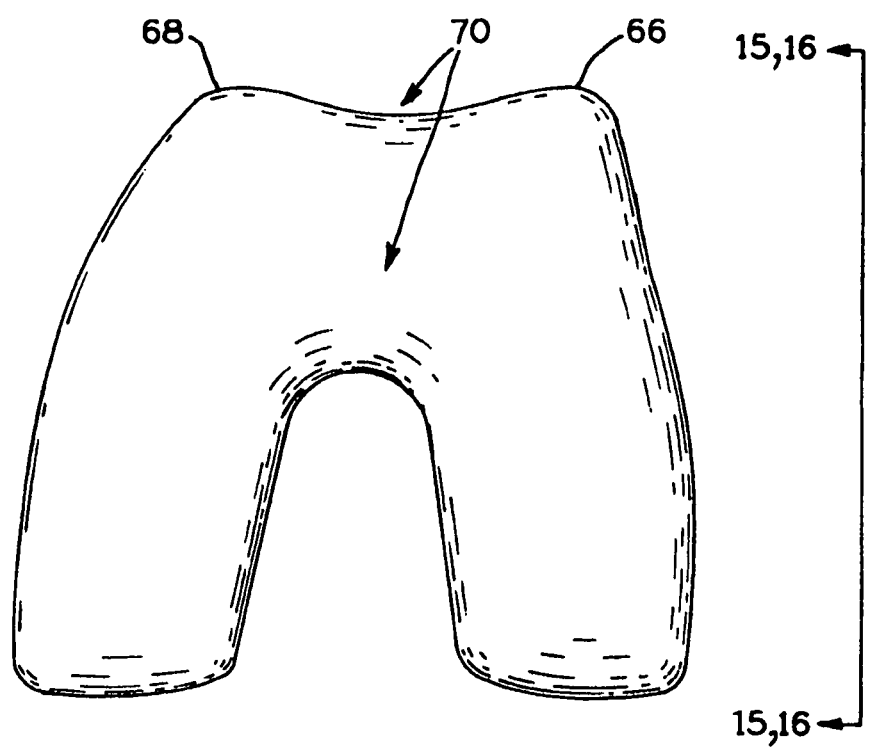
FIG. 14 is a distal view of an exemplary prosthesis.
Figure 15:
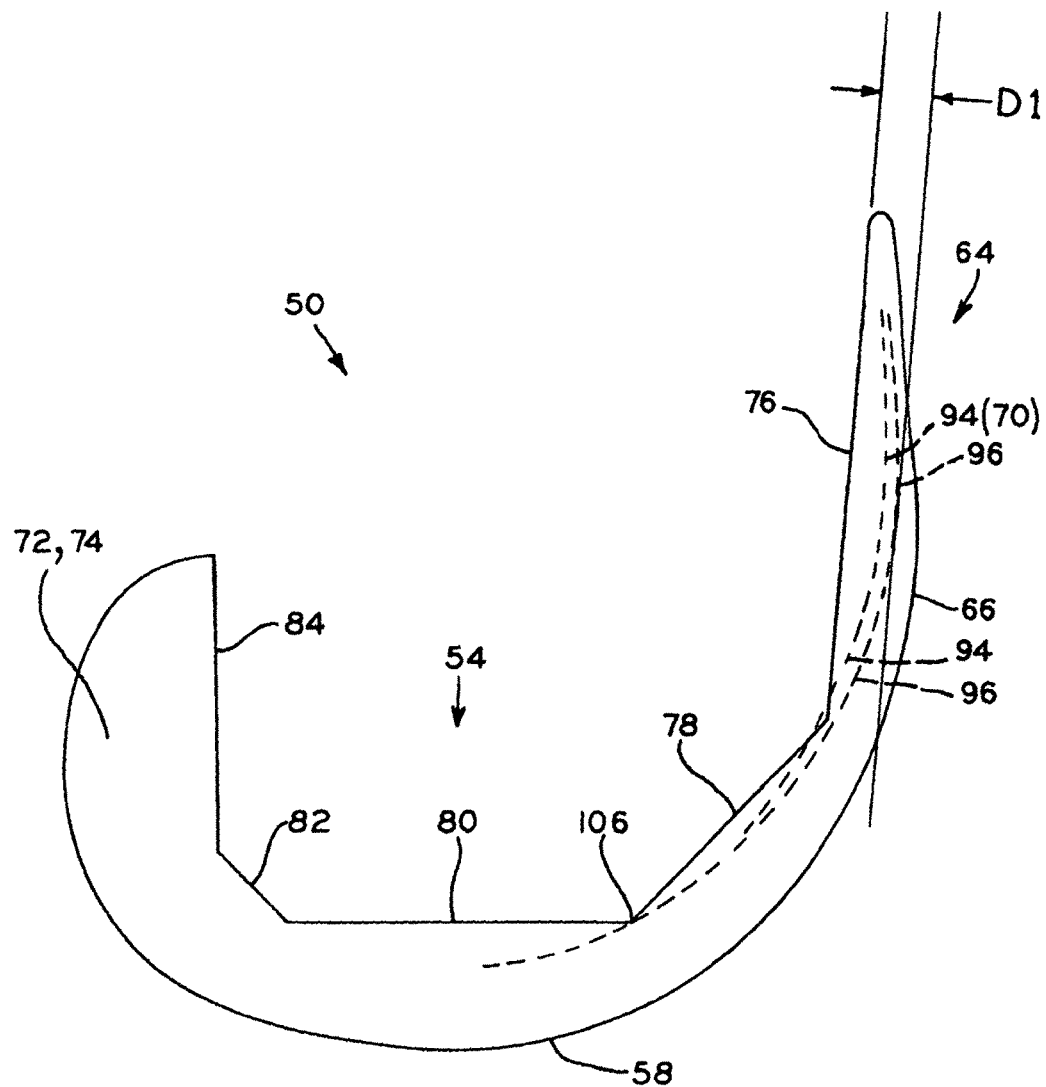
FIG. 15 is a side view of the prosthesis of FIG. 14, illustrating the recessed patellar sulcus thereof as compared with a known prosthesis.

Referring to FIG. 14, a distal view of prosthesis 50 is shown, including sulcus 70 disposed between lateral and medial anterior condyles 66 and 68, respectively. FIG. 15 is a side view of prosthesis 50, in which the anterior profile of sulcus 70 of prosthesis 50 in accordance with the present invention is shown as curve 94, and the anterior profile of the sulcus of a known prosthesis is represented by curve 96. A line parallel to non-articular anterior surface 76 and tangent to curve 94 or 96 at an anterior most point thereof may be used to define dimension D1. Dimension D1 represents the maximum thickness of sulcus 70, i.e., the width of sulcus 70 between non-articular anterior surface 76 and an anterior most point along curve 94 or curve 96. As may be seen from FIG. 15, curve 94 of sulcus 70 of prosthesis 50 is recessed, or shifted posteriorly, as compared to curve 96 of the sulcus of a known prosthesis, wherein dimension D1 of prosthesis 50 is less than dimension D1 of the known prosthesis. Advantageously, recessing the patellar sulcus 70 of prostheses 50 will allow the patella to articulate slightly more posterior than in known prostheses which will reduce the likelihood of the thickness of the patellar sulcus to be greater than the thickness of the femoral bone which is resected when the joint is in extension and early flexion.

Figure 16:
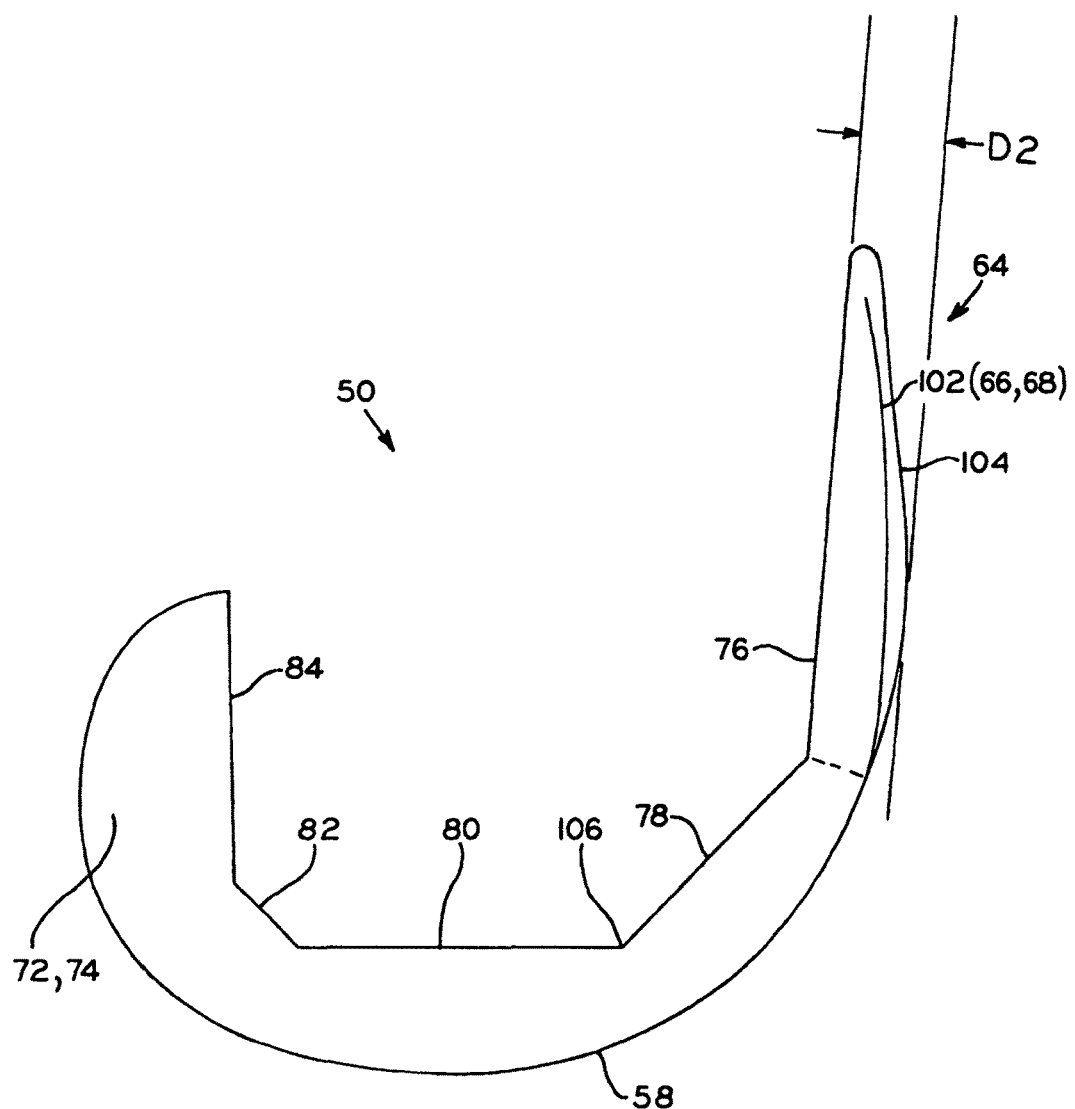
FIG. 16 is another side view of the prosthesis of FIG. 14, illustrating the reduced profile of the anterior condyles thereof as compared with a known prosthesis.

Referring to FIG. 16, the anterior profile of lateral or medial anterior condyle 66 or 68 of prosthesis 50 in accordance with the present invention is shown as curve 102, and the anterior profile of an anterior condyle of a known prosthesis is shown as curve 104. Dimension D2 represents the maximum thickness, or depth, of one or both of the lateral and medial anterior condyles between non-articular anterior surface 76 and a line drawn parallel to surface 76 and tangent to curve 102 or curve 104 at an anterior most point thereof. As may be seen from FIG. 16, curve 102 of at least one of the lateral and medial anterior condyles 66 and 68 of prosthesis 50 is recessed, or shifted posteriorly, as compared to curve 104 of the anterior condyles of a known prosthesis, wherein dimension D2 of prosthesis 50 is less than dimension D2 of the known prosthesis. Advantageously, the reduction of the anterior flange condyle thickness reduces the anterior flange profile and creates smoother, less abrupt changes in geometry as the condyles blend to the edges of the components while maintaining adequate height to prevent subluxation of the patella.

In Table 13 below, dimensions D1 and D2 described above are shown in accordance with a set of prostheses 50 (Embodiment 5) compared to a known set of prostheses (Conventional 5), as well as the differences between dimensions D1 and D2 of the present prosthesis and known prosthesis. Unless otherwise indicated, all numerical dimensional values presented herein are in millimeters ("mm").

TABLE 13

| SIZE | Embodiment 5 | | Conventional 5 | | Differences (Conventional 5 − Embodiment 5) | |
| --- | --- | --- | --- | --- | --- | --- |
| | "D1" | "D2" | "D1" | "D2" | "D1" | "D2" |
| C | 2.5 | 5.1 | 3.5 | 6.3 | 1.0 | 1.1 |
| D | 2.5 | 5.3 | 3.6 | 6.4 | 1.0 | 1.1 |
| E | 2.6 | 5.0 | 3.6 | 6.2 | 1.1 | 1.2 |
| F | 2.5 | 5.3 | 3.6 | 6.4 | 1.1 | 1.1 |
| G | 3.2 | 6.4 | 4.2 | 7.3 | 1.1 | 0.9 |

As may be seen from Table 13, the sulcus and condyle thicknesses D1 and D2 respectively, of prostheses of Embodiment 5 are considerably reduced as compared to the known prostheses (Conventional 5). In particular, the sulcus thickness D1 of an exemplary embodiment may range from about 2.5 mm to 3.2 mm and the condyle thickness D2 may range from about 5.0 mm to 6.4 mm. In exemplary embodiments, the sulcus thickness D1 of prostheses 50 may be as small as approximately 2.5, 2.6, 2.7, or 2.8 mm or as large as approximately 3.2, 3.1, 3.0, or 2.9 mm. In exemplary embodiments, the condyle thickness D2 of prostheses 50 may be as small as approximately 4.0, 4.3, 4.7, 5.0, 5.2, 5.4, or 5.6 mm or as large as approximately 6.4, 6.2, 6.1, 6.0, or 5.8 mm. As such, in an example, a ratio of the maximum condylar thickness D2 to the maximum sulcus thickness D1 can be in the range of 1.92:1 to 2.12:1, as is evident from Table 13. In another example, the maximum thickness D2 of the condyle is 1.92 to 2.12 times greater than the maximum thickness D1 of the sulcus, as is evident from Table 13. In yet another example, the maximum patellar sulcus thickness D1 of Embodiment 5 is less than the maximum patellar sulcus thickness D1 of Conventional 5 by 23.8 percent to 30.6 percent and the maximum condylar thickness D2 of Embodiment 5 is less than the maximum condylar thickness D2 of Conventional 5 by 12.3 percent to 19.4 percent, as is evident from Table 13.

The present prostheses further include a modified patellar sulcus tracking to further optimize conformance of the prostheses with female anatomy. The Q-angle ("quadriceps angle") is formed in the frontal plane by a pair of line segments, one extending from the tibial tubercle to the middle of the patella and the other extending from the middle of the patella to the anterior superior iliac spine (ASIS). In adults, the Q-angle is typically 14° for males and 17° for females, wherein the Q-angle for females is approximately 3° more lateral than that of males. Responsive to this observation, and as described in detail below, the end point of the patellar sulcus 70 of prostheses 50 is shifted 3° laterally with respect to known prostheses, i.e., in an exemplary embodiment, lateralization angle 108 is approximately 7° in FIG. 17A and approximately 10° in FIG. 17B.

Figure 17B:
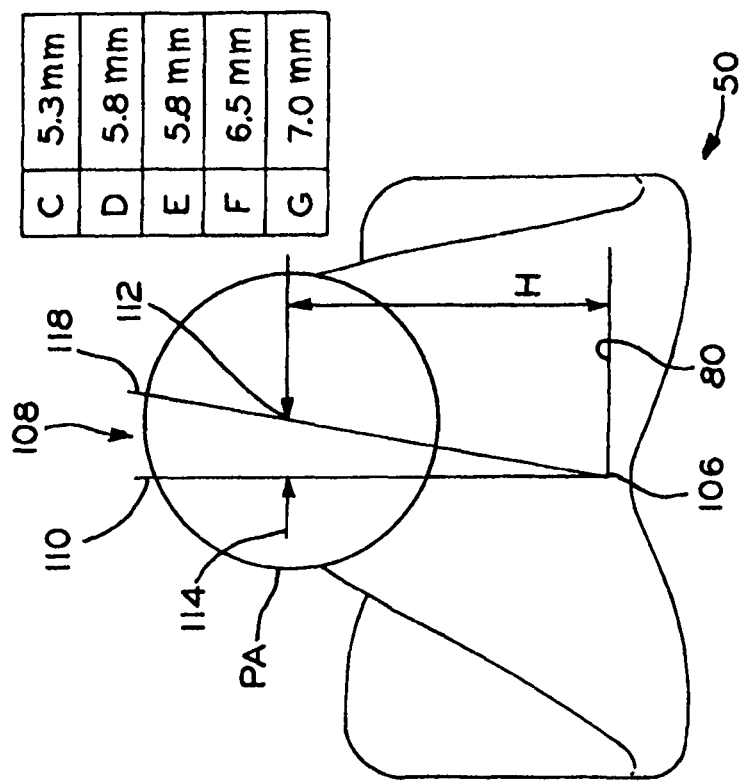
FIG. 17B is an A/P view of an exemplary prosthesis in accordance with the present invention having a more lateralized sulcus tracking.
Figure 17A:
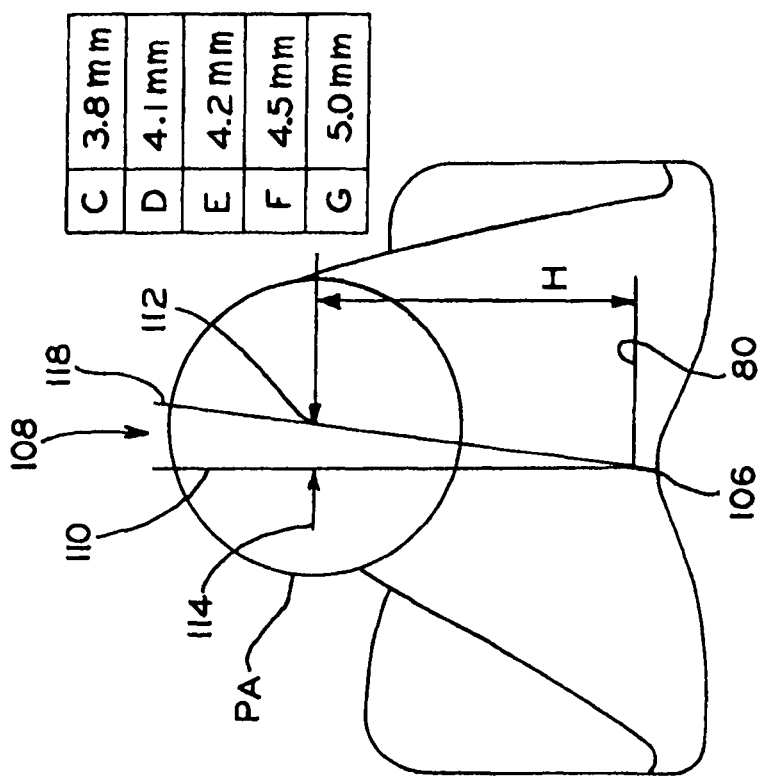
FIG. 17A is an A/P view of a known prosthesis having conventional sulcus tracking.

FIGS. 17A and 17B show A/P views of a known prosthesis and prosthesis 50, respectively, with simulated patellas shown in FIGS. 17A and 17B as circular structures "PA" superimposed upon the anterior flanges of the prostheses. During articulation of the prosthesis, the patella will track within the patellar sulcus of the prosthesis. Referring to FIGS. 15, 17A, and 17B, the vertex 106 of lateralization angle 108 (FIGS. 17A and 17B) is located at the intersection of a plane coincident with the flat, distal non articular surface 80 (FIG. 15) of prosthesis 50 with curve 94 (FIG. 15) of the patellar sulcus 70. From vertex 106, line 110 is drawn orthogonal to distal non articular surface 80, and the end point 112 of the patellar sulcus 70 is defined as the center of the patellar sulcus 70 at a line 114 parallel to distal non articular surface 80 and disposed at varying heights "H" in accordance with varying prosthesis size. Line 118 connects vertex 106 with end point 112 of the patellar sulcus and the angle originating at vertex 106 between lines 110 and 118 is lateralization angle 108. For a range of sizes C through G of prostheses represented in FIGS. 17A and 17B having varying height dimensions "H" indicated in Table 14 below between distal non articular surface 80 and line 114, the distance between line 110 and point 112, i.e., the lateralization distance, also varies as indicated in FIGS. 17A and 17B, wherein the foregoing data is summarized below in Table 14 for a known prosthesis (Conventional 1, FIG. 17A) and prosthesis 50 (Embodiment 1, FIG. 17B). Unless otherwise indicated, all numerical dimensional values presented herein are in millimeters ("mm").

TABLE 14

| Size | Vertical Position Height From Distal Face (H) | Lateralization Distance | | Change |
|---|---|---|---|---|
| | | Conventional 1 (FIG. 17A) | Embodiment 1 (FIG. 17B) | Conventional 1 – Embodiment 1 |
| C | 28.6 | 3.8 | 5.3 | 1.5 |
| D | 31.3 | 4.1 | 5.8 | 1.7 |
| E | 31.3 | 4.2 | 5.8 | 1.6 |
| F | 34.8 | 4.5 | 6.5 | 2.0 |
| G | 38.8 | 5.0 | 7.0 | 2.0 |

As may be seen from Table 14, the lateralization distance of prostheses 50 is increased with respect to known prostheses to optimize patella tracking with the prostheses to more closely conform to female anatomy. In an exemplary embodiment, the lateralization distance is greater than 5.0 mm. In an exemplary embodiment, the lateralization distance for prostheses 50 may be as small as approximately 5.0, 5.3, 5.6, or 5.9 mm or as large as approximately 7.0, 6.7, 6.4, or 6.1 mm.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A distal femoral prosthesis, comprising:
a distal portion including a planar distal non-articular surface and an opposing distal articular surface; and
an anterior portion including lateral and medial anterior condyles each defining an anterior articular surface, a patellar sulcus defined between said condyles, and an anterior non-articular surface, said patellar sulcus having a maximum thickness between 2.5 mm and 3.2 mm between an anterior most point on said sulcus and said anterior non-articular surface, and at least one of said condyles having a maximum thickness between 5.0 mm and 6.4 mm between an anterior most point on said anterior articular surface of said condyle and said anterior non-articular surface;
wherein a ratio of the maximum condylar thickness to the maximum patellar sulcus thickness is in the range of 1.92:1 to 2.12:1.

2. The distal femoral prosthesis of claim 1, wherein said maximum thickness of said patellar sulcus is in the range of 2.6 mm to 3.1 mm.

3. The distal femoral prosthesis of claim 1, wherein said maximum thickness of said patellar sulcus is 3.2 mm.

4. The distal femoral prosthesis of claim 1, further comprising medial and lateral posterior condyles each having a posterior non-articular surface.

5. The distal femoral prosthesis of claim 4, further comprising:
a distal anterior non-articular surface connecting said planar distal non-articular surface and said anterior non-articular surfaces; and
distal posterior non-articular surfaces connecting said planar distal non-articular surface and said posterior non-articular surfaces.

6. A distal femoral prosthesis, comprising:
a distal portion including a planar distal non-articular surface and an opposing distal articular surface;
an anterior portion including lateral and medial anterior condyles each defining an anterior articular surface, and an anterior non-articular surface, at least one of said condyles having a maximum thickness between 5.0 mm and 6.4 mm between an anterior most point on said anterior articular surface of said condyle and said anterior non-articular surface; and
a patellar sulcus defined between said condyles, said patellar sulcus having a maximum thickness between an anterior most point on said sulcus and said anterior non-articular surface, wherein said maximum thickness of said condyles is 1.92 to 2.12 times greater than said maximum thickness of said sulcus.

7. The distal femoral prosthesis of claim 6, wherein said maximum thickness of the at least one of said condyles is in the range of 5.0 mm to 6.1 mm.

8. The distal femoral prosthesis of claim 6, wherein said maximum thickness of the at least one of said condyles is 5.0 mm.

9. The distal femoral prosthesis of claim 6, wherein said maximum thickness of the at least one of said condyles is 6.4 mm.

10. The distal femoral prosthesis of claim 6, wherein said maximum thickness of the at least one of said condyles is in the range of 5.2 mm to 6.0 mm.

11. The distal femoral prosthesis of claim 6, wherein said maximum thickness of the at least one of said condyles is 5.3 mm.

12. The distal femoral prosthesis of claim 6, further comprising medial and lateral posterior condyles each having a posterior non-articular surface.

13. The distal femoral prosthesis of claim 12, further comprising:
a distal anterior non-articular surface connecting said planar distal non-articular surface and said anterior non-articular surfaces; and
distal posterior non-articular surfaces connecting said planar distal non-articular surface and said posterior non-articular surfaces.

14. A set of distal femoral prostheses comprising:
a first distal femoral prosthesis comprising:
a first distal portion including a first distal articular surface and a first planar distal non-articular surface; and
a first anterior portion including first lateral and medial anterior condyles each defining a first anterior articular surface, a first patellar sulcus defined between said condyles, and a first anterior non-articular surface, said first patellar sulcus having a first thickness defined between an anterior most point on said first patellar sulcus and said first anterior non-articular surface; and
a second distal femoral prosthesis comparable in overall size to said first distal femoral prosthesis, said second distal femoral prosthesis comprising:
a second distal portion including a second distal articular surface and a second planar distal non-articular surface; and
a second anterior portion including second lateral and medial anterior condyles each defining a second anterior articular surface, a second patellar sulcus defined between said condyles, and a second anterior non-articular surface, said second patellar sulcus having a second thickness defined between an anterior most point on said second patellar sulcus and said second anterior non-articular surface, wherein said second thickness is less than said first thickness by 23.8 percent to 30.6 percent, and wherein at least one of said first lateral and medial anterior condyles of said first distal femoral prosthesis has a third thickness defined between an anterior most point on said first anterior articular surface of said first lateral or medial condyle and said first anterior non-articular surface, at least one of said second lateral and medial anterior condyles of said second distal femoral prosthesis has a fourth thickness defined between an anterior most point on said second anterior articular surface of said second lateral or medial condyle and said second anterior non-articular surface, and said fourth thickness is less than said third thickness by 12.3 percent to 19.4 percent.

15. The set of distal femoral prostheses of claim 14, wherein said second thickness is in the range of 2.5 mm to 3.2 mm.

16. The set of distal femoral prostheses of claim 14, wherein said fourth thickness is in the range of 5.0 mm to 6.4 mm.

17. The set of distal femoral prostheses of claim 14, wherein said second thickness is less than said first thickness by at least 24 percent.

18. The set of distal femoral prosthesis of claim 14, wherein said second thickness is less than said first thickness by no more than 30 percent.

* * * * *

UNITED STATES PATENT AND TRADEMARK OFFICE
CERTIFICATE OF CORRECTION

PATENT NO. : 9,592,127 B2
APPLICATION NO. : 11/611021
DATED : March 14, 2017
INVENTOR(S) : Earl et al.

Page 1 of 1

It is certified that error appears in the above-identified patent and that said Letters Patent is hereby corrected as shown below:

On the Title Page

On page 4, in Column 2, under "Other Publications", Line 7, before "filed", insert --Application--

On page 5, in Column 2, under "Other Publications", Line 1, before "Canadian", delete "1"

Signed and Sealed this
Fourteenth Day of August, 2018

Andrei Iancu
*Director of the United States Patent and Trademark Office*